United States Patent
Tokarchuk et al.

(10) Patent No.: US 11,737,841 B2
(45) Date of Patent: Aug. 29, 2023

(54) CONFIGURING SURGICAL SYSTEM WITH SURGICAL PROCEDURES ATLAS

(71) Applicant: Intuitive Surgical Operations, Inc., Sunnyvale, CA (US)

(72) Inventors: Brent Tokarchuk, San Carlos, CA (US); Mahdi Azizian, Santa Clara, CA (US); Joey Chau, Cupertino, CA (US); Simon P. DiMaio, San Carlos, CA (US); Brian D. Hoffman, Mountain View, CA (US); Anthony M. Jarc, Duluth, GA (US); Henry C. Lin, San Jose, CA (US); Ian E. McDowall, Woodside, CA (US); William C. Nowlin, Los Altos Hills, CA (US); John D. Seaman, II, San Jose, CA (US); Jonathan M. Sorger, Belmont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 31 days.

(21) Appl. No.: 17/354,567

(22) Filed: Jun. 22, 2021

(65) Prior Publication Data
US 2021/0315650 A1    Oct. 14, 2021

Related U.S. Application Data

(63) Continuation of application No. 15/735,164, filed as application No. PCT/US2016/036733 on Jun. 9, 2016, now Pat. No. 11,058,501.
(Continued)

(51) Int. Cl.
*A61B 34/35*    (2016.01)
*A61B 34/10*    (2016.01)
(Continued)

(52) U.S. Cl.
CPC .............. *A61B 34/35* (2016.02); *A61B 34/00* (2016.02); *A61B 34/10* (2016.02); *A61B 34/37* (2016.02);
(Continued)

(58) Field of Classification Search
CPC ......... A61B 34/35; A61B 34/00; A61B 34/10; A61B 34/37; A61B 34/76; A61B 34/77;
(Continued)

(56) References Cited

U.S. PATENT DOCUMENTS 4,887,222 A * 12/1989 Miyake .................. G05B 19/41
700/262
5,704,791 A    1/1998 Gill
(Continued)

FOREIGN PATENT DOCUMENTS

CA    2929282 A1    5/2015
CN    102362302 A    2/2012
(Continued)

OTHER PUBLICATIONS

Extended European Search Report for Application No. 16808303.8, dated May 20, 2019, 14 pages.
(Continued)

*Primary Examiner* — Jeff A Burke
*Assistant Examiner* — Kyle T Johnson
(74) *Attorney, Agent, or Firm* — Schwegman, Lundberg & Woessner, P.A.

(57) ABSTRACT

A surgical method is provided for use with a teleoperated surgical system (surgical system), the method comprising: recording surgical instrument kinematic information indicative of surgical instrument motion produced within the surgical system during the occurrence of the surgical procedure; determining respective kinematic signatures associated with respective surgical instrument motions; producing
(Continued)

an information structure in a computer readable storage device that associates respective kinematic signatures with respective control signals; comparing, during a performance of the surgical procedure surgical instrument kinematic information during the performance with at least one respective kinematic signature; launching, during a performance of the surgical procedure an associated respective control signal in response to a match between surgical instrument kinematics during the performance and a respective kinematic signature.

19 Claims, 13 Drawing Sheets

Related U.S. Application Data

(60) Provisional application No. 62/173,077, filed on Jun. 9, 2015.

(51) Int. Cl.

| | | |
|---|---|---|
| *A61B 34/00* | (2016.01) | |
| *A61B 90/00* | (2016.01) | |
| *A61B 34/37* | (2016.01) | |
| *G16H 50/50* | (2018.01) | |
| *B25J 9/16* | (2006.01) | |
| *G16H 20/40* | (2018.01) | |
| *G16H 40/67* | (2018.01) | |
| *A61B 34/20* | (2016.01) | |

(52) U.S. Cl.
CPC .............. *A61B 34/76* (2016.02); *A61B 34/77* (2016.02); *A61B 90/00* (2016.02); *B25J 9/1689* (2013.01); *G16H 20/40* (2018.01); *G16H 40/67* (2018.01); *G16H 50/50* (2018.01); *A61B 34/20* (2016.02); *A61B 90/361* (2016.02); *A61B 90/37* (2016.02); *A61B 2090/3612* (2016.02); *G05B 2219/40134* (2013.01); *G05B 2219/40137* (2013.01); *G05B 2219/40143* (2013.01); *G05B 2219/40144* (2013.01); *G05B 2219/40161* (2013.01); *G05B 2219/40167* (2013.01); *G05B 2219/40168* (2013.01); *G05B 2219/40169* (2013.01); *G05B 2219/40191* (2013.01); *G05B 2219/45118* (2013.01)

(58) Field of Classification Search
CPC ....... A61B 90/00; A61B 34/20; A61B 90/361; A61B 90/37; A61B 2090/3612; A61B 34/70; A61B 2034/107; A61B 2090/374; A61B 2090/376; A61B 2090/3762; B25J 9/1689; G05B 2219/40134; G05B 2219/40137; G05B 2219/40143; G05B 2219/40144; G05B 2219/40161; G05B 2219/40167; G05B 2219/40168; G05B 2219/40169; G05B 2219/40191; G05B 2219/45118; G16H 20/40; G16H 40/67; G16H 50/50
See application file for complete search history.

(56) References Cited

U.S. PATENT DOCUMENTS

| | | | |
|---|---|---|---|
| 5,769,640 A | 6/1998 | Jacobus et al. | |
| 6,074,213 A | 6/2000 | Hon | |
| 6,573,889 B1 | 6/2003 | Georgiev | |
| 7,236,618 B1 | 6/2007 | Chui et al. | |
| 8,317,744 B2 | 11/2012 | Kirschenman | |
| 8,663,122 B2 | 3/2014 | Schecter | |
| 8,992,230 B2 | 3/2015 | Tuchschmid et al. | |
| 9,161,817 B2 | 10/2015 | Olson et al. | |
| 9,196,176 B2 | 11/2015 | Hager et al. | |
| 9,268,915 B2 | 2/2016 | Holmes et al. | |
| 9,341,704 B2 | 5/2016 | Picard et al. | |
| 9,652,591 B2 | 5/2017 | Moctezuma De La Barrera et al. | |
| 10,912,619 B2 | 2/2021 | Jarc et al. | |
| 11,058,501 B2 | 7/2021 | Tokarchuk et al. | |
| 2003/0029463 A1 | 2/2003 | Niemeyer | |
| 2003/0216715 A1 | 11/2003 | Moll et al. | |
| 2004/0106916 A1* | 6/2004 | Quaid ................... A61B 34/71 606/1 |
| 2006/0142657 A1* | 6/2006 | Quaid ................... A61B 90/37 600/424 |
| 2009/0017430 A1 | 1/2009 | Muller-Daniels et al. | |
| 2009/0036775 A1 | 2/2009 | Ikuma et al. | |
| 2009/0036902 A1 | 2/2009 | Dimaio et al. | |
| 2009/0088634 A1 | 4/2009 | Zhao et al. | |
| 2010/0191071 A1 | 7/2010 | Anderson et al. | |
| 2010/0248200 A1 | 9/2010 | Ladak et al. | |
| 2011/0046476 A1 | 2/2011 | Cinquin et al. | |
| 2011/0267450 A1 | 11/2011 | Pronkine | |
| 2011/0295247 A1 | 12/2011 | Schlesinger et al. | |
| 2011/0305379 A1 | 12/2011 | Mahfouz | |
| 2012/0178069 A1 | 7/2012 | McKenzie et al. | |
| 2013/0041368 A1 | 2/2013 | Cunningham et al. | |
| 2013/0237811 A1 | 9/2013 | Mihailescu et al. | |
| 2013/0307955 A1* | 11/2013 | Deitz ................... A61B 5/4566 348/77 |
| 2013/0331859 A1 | 12/2013 | Kumar et al. | |
| 2014/0005684 A1 | 1/2014 | Kim et al. | |
| 2014/0039517 A1* | 2/2014 | Bowling ................ B25J 9/161 606/130 |
| 2014/0046128 A1 | 2/2014 | Lee et al. | |
| 2014/0081659 A1* | 3/2014 | Nawana ............... A61B 5/4833 705/3 |
| 2014/0107471 A1* | 4/2014 | Haider ................. A61B 5/1076 606/82 |
| 2014/0199673 A1 | 7/2014 | Jian et al. | |
| 2014/0200440 A1* | 7/2014 | Iannotti .................. A61B 34/20 600/424 |
| 2014/0228860 A1 | 8/2014 | Steines et al. | |
| 2014/0272867 A1 | 9/2014 | Ratcliffe et al. | |
| 2014/0276943 A1 | 9/2014 | Bowling et al. | |
| 2014/0287393 A1 | 9/2014 | Kumar et al. | |
| 2014/0343913 A1* | 11/2014 | Avisar ................... A61B 90/37 703/11 |
| 2014/0379132 A1 | 12/2014 | Fudaba et al. | |
| 2015/0298318 A1 | 10/2015 | Wang et al. | |
| 2015/0356252 A1* | 12/2015 | Beker .................... G16H 50/70 705/3 |
| 2016/0098933 A1 | 4/2016 | Reiley et al. | |
| 2016/0106616 A1 | 4/2016 | Kim et al. | |
| 2016/0157832 A1 | 6/2016 | Kang et al. | |
| 2017/0367766 A1* | 12/2017 | Mahfouz .............. A61B 17/155 |
| 2018/0153505 A1 | 6/2018 | Cadieu et al. | |
| 2018/0153632 A1* | 6/2018 | Tokarchuk ............ A61B 34/10 |
| 2018/0345557 A1* | 12/2018 | Kang .................. B29C 45/4225 |
| 2019/0029766 A1* | 1/2019 | Griffiths ................ A61B 34/35 |
| 2021/0186634 A1 | 6/2021 | Jarc et al. | |
| 2021/0282804 A1 | 9/2021 | Worrell et al. | |
| 2021/0315650 A1* | 10/2021 | Tokarchuk ............ G16H 40/67 |

FOREIGN PATENT DOCUMENTS

| | | |
|---|---|---|
| CN | 101160104 B | 7/2012 |
| CN | 103249368 A | 8/2013 |
| CN | 103705306 A | 4/2014 |
| CN | 103961178 A | 8/2014 |
| CN | 104203078 A | 12/2014 |
| CN | 104271046 A | 1/2015 |
| CN | 104582624 A | 4/2015 |
| CN | 104661612 A | 5/2015 |
| EP | 1356781 A2 | 10/2003 |
| EP | 1443416 A1 | 8/2004 |
| JP | 2000287986 A | 10/2000 |
| JP | 2003150569 A | 5/2003 |

(56) References Cited

FOREIGN PATENT DOCUMENTS

| JP | 2007534351 A | 11/2007 |
|---|---|---|
| JP | 2012065698 A | 4/2012 |
| JP | 2013543764 A | 12/2013 |
| KR | 20150047478 A | 5/2015 |
| WO | WO-2006091494 A1 | 8/2006 |
| WO | WO-2010039394 A1 | 4/2010 |
| WO | WO-2012065175 A2 | 5/2012 |
| WO | WO-2012158324 A2 | 11/2012 |
| WO | WO-2014005139 A2 | 1/2014 |
| WO | WO-2014139021 A1 | 9/2014 |
| WO | WO-2015066565 A1 | 5/2015 |
| WO | WO-2015095715 A1 | 6/2015 |
| WO | WO-2016201123 A1 | 12/2016 |
| WO | WO-2017083768 A1 | 5/2017 |

OTHER PUBLICATIONS

Extended European Search Report for Application No. 16865162.8 dated Jul. 3, 2019, 11 pages.
International Preliminary Report on Patentability for Application No. PCT/US2016/036733, dated Dec. 21, 2017, 11 pages.
International Preliminary Report on Patentability for Application No. PCT/US2016/061694, dated May 24, 2018, 6 pages.
International Search Report and Written Opinion for Application No. PCT/US16/36733, dated Oct. 12, 2016, 15 pages.
International Search Report and Written Opinion for Application No. PCT/US2016/061694, dated Feb. 20, 2017, 10 pages.
Lalys F., et al., "A Framework for the Recognition of High-Level Surgical Tasks from Video images for Cataract Surgeries," IEEE Transactions on Bio-medical Engineering, Apr. 2012, vol. 59 (4), pp. 966-976.
Office Action dated Apr. 27, 2020 for Chinese Application No. 201680038267 filed Jun. 9, 2016, 29 pages.
Partial Supplementary European Search Report for Application No. 18808303.8, dated Jan. 28, 2019, 16 pages.
Reiley C.E., et.al., "Motion Generation of Robotic Surgical Tasks: Learning from Expert Demonstrations," Annual International Conference of the IEEE Engineering in Medicine and Biology, 2010, pp. 1-9.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Voros S., et al., "Towards "Real-time" Tool-tissue Interaction Detection in Robotically Assisted Laparoscopy," Proceedings of 2nd IEEE RAS & EMBS International Conference on Biomedical Robotics and Biomechatronics, Oct. 2008, pp. 562-567.
European Application for Serial No. EP16865162.8, Communication Pursuant to Article 94(3) EPC dated May 10, 2023, 09 pages.

* cited by examiner

| Surgery Type 1006-1 | Patient EHR 1006-2 | Physician Information 1006-3 | System Information 1006-4 | Recordings 1006-5 | Annot. 1006-6 |
1006
FIG. 11
| $t_1$ | $MPI_1$ | $KIN_1$ | $Astate_1$ | $Annot_1$ |
| $t_2$ | $MPI_2$ | $KIN_2$ | $Astate_2$ | $Annot_2$ |
| ⋮ | ⋮ | ⋮ | ⋮ | ⋮ |
| $t_n$ | $MPI_n$ | $KINn$ | $Astate_n$ | $Annot_n$ |
1008
FIG. 12
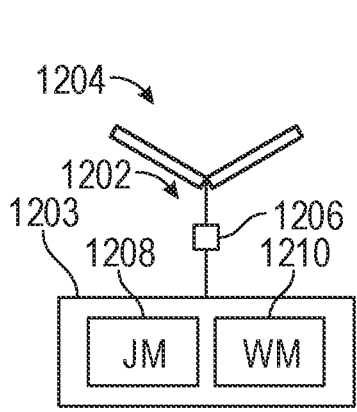
FIG. 13A
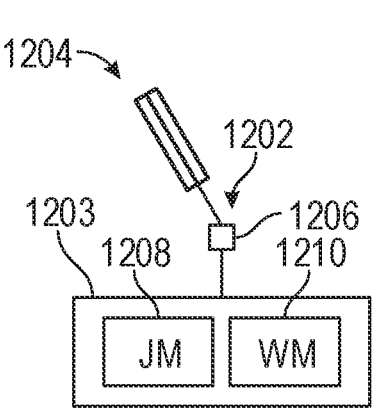
FIG. 13B
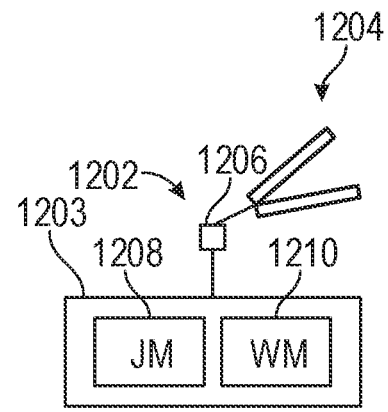
FIG. 13C

CONFIGURING SURGICAL SYSTEM WITH SURGICAL PROCEDURES ATLAS

CROSS-REFERENCE TO RELATED APPLICATIONS

This application is a continuation of and claims the benefit of priority under 35 U.S.C. § 120 to U.S. patent application Ser. No. 15/735,164, filed on Dec. 9, 2017, which is a U.S. National Stage Filing under 35 U.S.C. 371 from International Application No. PCT/US2016/036733, filed on Jun. 9, 2016, and published as WO 2016/201123 A1 on Dec. 15, 2016, which claims the benefit of priority under 35 U.S.C. § 119(e) to U.S. Provisional Patent Application No. 62/173,077, filed on Jun. 9, 2015, each of which is hereby incorporated by reference herein in its entirety.

BACKGROUND

1. Field of Invention

Inventive aspects are associated with medical devices used during surgery. More specifically, aspects are associated with controlling a surgical instrument in a robot-assisted surgical system based upon kinematic information and anatomical tissue image information from prior surgical procedures.

2. Art

Surgeons typically undertake extensive study before performing a surgical procedure. Traditionally, surgeons were limited to the study of generic anatomical models, such as photographs or drawings. More recently, various pre-operative diagnostic procedures (e.g., x-ray, CT, MRI, etc.) have made patient-specific anatomical information available.

In some cases, it is desirable to make additional, relevant anatomic and surgical procedure information available to a surgeon. In one aspect, it is desirable to provide a surgeon planning an operation on a particular patient with a surgical site video recording of an earlier surgical procedure performed on the particular patient. In another aspect, it is desirable to provide a surgeon with one or more surgical video recordings of surgical procedures on other patients that are similar to the surgical procedure planned for a particular patient. In one aspect, it is desirable to provide such information to a surgeon prior to the surgeon undertaking a particular surgical procedure. And in another aspect, it may be desirable to provide this information to a surgeon intraoperatively.

In one aspect, it is desirable to configure a video database that includes intraoperative surgical site video recordings of various procedures undergone by various patients. In one aspect, it is desirable to configure a medical device capable of video recording to further include an input that enables a surgeon using the medical device to highlight and annotate the video recording in real time as it is being recorded. In one aspect, it is desirable to configure a computer-based pattern matching algorithm to search through the individual records of the video database, identify relevant video records, and provide a surgeon with this relevant information for a particular surgical procedure.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

In one aspect, a method is provided for use with a teleoperated surgical system. Surgical instrument kinematic information that is indicative of surgical instrument motion is recorded for multiplicity of occurrences of a surgical procedure. Kinematic signatures are determined based upon the recorded kinematic information that are representative of surgical instrument motions. An information structure is produced in computer readable storage device that associates respective kinematic signatures with respective electronic control signals for a surgical system. During performance of a surgical procedure using a surgical system, surgical instrument kinematic information produced by the system during the procedure is compared with at least one kinematic signature. An electronic control signal associated with the at least one kinematic signature is launched within the surgical system in response to a match between kinematic information produced during the surgical procedure and a respective kinematic signature. More particularly, some system behavior is triggered based upon kinematic analysis.

In another aspect, a method is provided for use with a teleoperated surgical system. Motion picture images of a surgical scene that are produced during robot-assisted surgical procedure is recorded for multiplicity of occurrences of a surgical procedure. Surgical image signatures are determined based upon the recorded motion picture images. An information structure is produced in computer readable storage device that associates respective surgical image signatures with respective electronic control signals for a surgical system. During performance of a surgical procedure using a surgical system, motion picture images produced during the procedure are compared with at least one surgical image signature. An electronic control signal associated with the at least one surgical image signature is launched within the surgical system in response to a match between surgical images produced during the surgical procedure and a respective surgical image signature. More particularly, some system behavior is triggered based upon video analysis.

In another aspect, a training method is provided for use with a teleoperated surgical system. Motion picture images are recorded that show anatomical tissue within a surgical scene displayed within a viewer of a surgical system during a surgical procedure. Surgical system control haptics information, which is imparted to a surgical instrument control in response to a force imparted to a surgical instrument during contact with the displayed anatomical tissue, is recorded. The recorded motion picture images are replayed within a surgical system viewer during a simulation of the surgical procedure. The recorded surgical instrument control haptics are imparted to a surgical instrument control during the replaying of the recorded motion picture images during the simulation of the surgical procedure. In some embodiments, surgical control haptics are replayed through vibro-tactile stimulation of control inputs.

In another aspect, a training method is provided for use with a teleoperated surgical system. Diagnosis data information instance instances are recorded for each of many occurrences of a surgical procedure within a robot-assisted surgical system. Each diagnosis data information instance includes respective motion picture images of anatomical tissue within a surgical scene displayed within a viewer of a surgical system during a surgical procedure. Each diagnosis data information instance also includes surgical instrument control haptics imparted to a surgical instrument control in response to a force imparted to a surgical instrument during contact with the displayed anatomy during the surgical procedure. An information structure is produced in a computer readable storage device that associates respective diagnosis data information instances with respective diagnoses. A respective diagnosis data information instance is selected. Recorded motion picture images from the selected respective recorded diagnosis data information instance are replayed within a surgical system viewer during a simulation of the surgical procedure. Recorded surgical instrument control haptics information from the selected respective recorded diagnosis data information instance is imparted to a surgical instrument control during the replaying of the recorded motion picture images during the simulation of the surgical procedure.

In another aspect, a teleoperated surgical system includes an information structure in a computer readable storage device that associates surgical image signatures with control signals. A processor is configured to compare surgical images produced within a surgical scene during a surgical procedure with at least one surgical image signature. The processor is configured to launch a control signal in response to a match between the surgical images and the at least one surgical image signature. An instrument is configured to adjust its motion in response to the control signal.

In another aspect, a teleoperated surgical system includes an information structure in a computer readable storage device that associates respective surgical image signatures with respective control signals. A processor is configured to compare surgical images within a surgical scene during a surgical procedure with at least one surgical image signature. The processor is configured to launch a control signal in response to a match between surgical images during the surgical procedure and the at least one surgical image signature. An instrument is configured to adjust its motion in response to the control signal.

BRIEF DESCRIPTION OF THE DRAWINGS

FIG. 11 is an illustrative drawing representing an example instance of a first data information structure included within the atlas, which includes information about an individual surgical procedure in accordance with some embodiments.

FIG. 12 is an illustrative drawing representing an example instance of the second data information structure included within the atlas, which associates recorded motion picture image segments from an individual surgical procedure, corresponding surgical instrument kinematics information segments, corresponding surgical system actuation states, and corresponding annotations, in accordance with some embodiments.

FIGS. 13A-13C are illustrative drawings showing an example surgical instrument and an actuator assembly in which the surgical instrument is shown in three different example instrument states in accordance with some embodiments.

DETAILED DESCRIPTION

Figure 1:
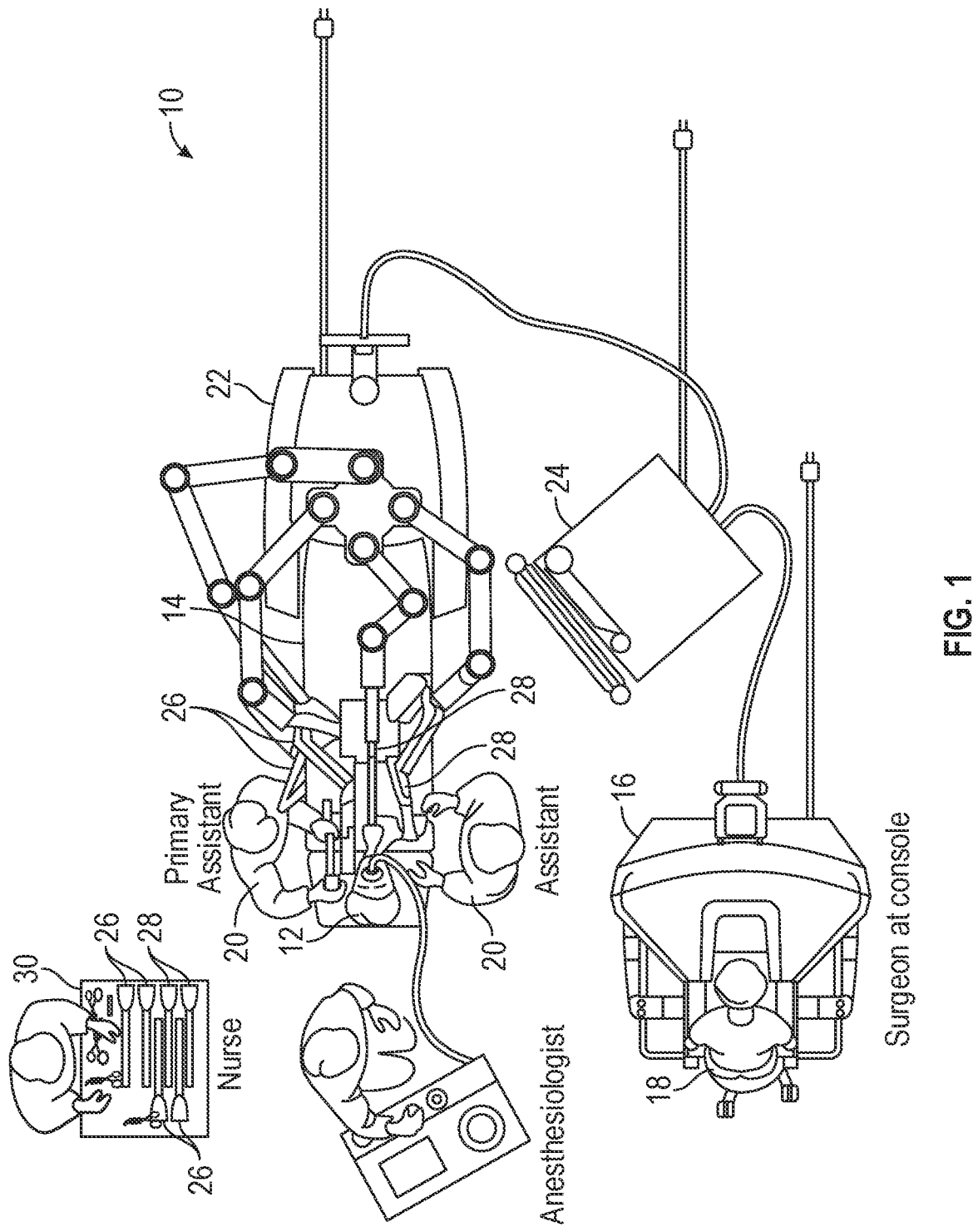
FIG. 1 is a plan view of a minimally invasive teleoperated surgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the scope of this description and the claims. In some instances, well-known circuits, structures, or to have not been shown or described in detail in order not to obscure the invention. Like numbers in two or more figures represent the same or similar elements.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® Surgical System (specifically, a Model IS4000, marketed as the da Vinci® Xi™ HD™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000 da Vinci® Xi™ Surgical System, the Model IS3000 da Vinci Si® Surgical System) are merely exemplary and are not to be considered as limiting the scope of the inventive aspects disclosed herein.

In accordance with various aspects, the present disclosure describes a surgical planning tool that includes a medical device configured to video record the performance of surgical procedures. The video recordings can be embedded with various metadata, e.g., highlights made by a medical person. Additionally, the video recordings can be tagged with various metadata, e.g., text annotations describing certain subject matter of the video, the identity of the patient to whom the video recording corresponds, biographical or medical information about the patient, and the like. In one aspect, tagged metadata is embedded in the video recordings.

In accordance with further aspects, information patterns are identified within motion picture images and surgical instrument kinematic information collected from numerous teleoperated surgical procedures. Motion picture information can indicate anatomical tissue geometry and coloration, for example. Kinematic information can indicate surgical instrument motion characteristics such as direction of instrument motion, speed and acceleration of instrument motion, and sequences of instrument motion, for example. The information patterns can be identified based upon the recorded motion picture and kinematic information can be used as a basis to manage or regulate control surgical instrument during surgery. The information patterns can be used as a basis to provide intra-surgical guidance to a surgeon.

In accordance with further aspects, motion picture images in concert with haptic feedback can be used as bases for surgical training. For example, a surgeon can re-experience a prior surgical procedure performed by that surgeon through a surgical simulation that replays motion picture images and corresponding haptic feedback produced during the prior surgery by that same surgeon. Alternatively, for example, a surgeon can experience a previous surgical procedure performed by a different surgeon through a surgical simulation that replays motion picture images and corresponding haptic feedback produced during that previous surgery by another. Thus, a surgeon can use a surgical simulation as an opportunity to refine surgical skills through a simulated practice surgery that replays an actual surgical experience by that surgeon or another surgeon of relationship between visual cues and haptic cues.

In accordance with still further aspects, proposed intra-surgical diagnoses are developed based upon information patterns identified within motion picture images and surgical instrument kinematic information collected from numerous teleoperated surgical procedures. A skilled surgeon often can evaluate tissue disease state and tissue trauma state based at least in part upon tissue geometry and coloration. Recorded motion pictures provide information as to tissue geometry and tissue coloration of anatomical tissue within a surgical scene within a surgical system. Moreover, a skilled surgeon can evaluate tissue disease state and tissue trauma state based at least in part upon palpation of the tissue. In a teleoperated surgical system, palpation of tissue can be achieved through touch upon a tissue structure using a surgeon-operated instrument control that provides haptic feedback to a surgeon operating the control that is indicative of reactive force imparted to the instrument in response to the instrument touch upon the tissue structure. Expert surgeon evaluation of the collected motion picture images and surgical instrument kinematic information is used to identify different patterns of images and kinematics indicative of different intra-surgical diagnoses. The video recordings and information structures that associate motion picture images with surgical instrument kinematics information can be archived on an electronic medical record database implemented locally or remotely (e.g., on a remote computer system on a LAN or WAN, or on a cloud data storage service). Similarly, in some embodiments, information structures that associate motion picture images with control haptics feedback information and corresponding diagnosis recommendations can be archived on an electronic medical record database implemented locally or remotely for use in surgeon training, for example. The video recordings and information structures can be made available to interested health care providers. In some embodiments, stored information structures can be made available for use with a teleoperated robot assisted surgical system to generate control signal information to provide to a surgical system to produce intra-surgery surgical guidance to a surgeon and to provide robot-assisted surgical control of instruments during a surgical procedure. In some embodiments, stored information structures can be made available for use with a surgical simulation system to replay surgical scenes and corresponding haptic feedback for use in surgeon training in mechanics of operating a surgical system. In some embodiments, stored information structures can be made available for use with a surgical simulation system to replay surgical scenes and corresponding haptic feedback for use in surgeon training in diagnosis of tissue structure disease state and tissue trauma state while performing a surgery using the surgical system.

Health care providers can search the medical device database based upon one or more of surgical procedures to be performed, tissue structure characteristics, and surgical instrument kinematics for videos and information structure relationships of interest using the metadata tags described above, for example. Additionally, in one aspect, the surgical planning tool includes a computer-based pattern matching and analysis algorithm. In one aspect, the pattern-matching algorithm culls through the videos stored on the electronic medical record database to identify correlations between visual characteristics in the video recordings and associated metadata tags made by medical persons. The surgical planning tool can apply these correlations to newly encountered anatomy, and thereby assist medical persons performing a procedure in making determinations about patient anatomy, preferred surgical approaches, disease states, potential complications, etc.

In another aspect, a pattern matching algorithm culls through recorded motion picture image information and, optionally, kinematic information to identify correlations between anatomical tissue features such as geometry and instrument motion, for example. Such patterns can be useful, for example, to identify kinds of anatomical features associated with kinds of instrument motion. Such patterns also can be useful, for example, to identify kinds of anatomical features that are not associated with kinds of instrument motion. Such pattern information can be used as a basis to produce surgical guidance to present to a surgeon during a surgery, for example. Such pattern information can be used as a basis to deter or to impart surgical certain surgical instrument motion during a surgery, for example.

In another aspect, a pattern matching algorithm culls through recorded motion picture image information and haptic feedback information to identify correlations between anatomical tissue features such as geometry and reactive force imparted by the tissue structure in response to touch by a surgical instrument, for example. Such patterns can be useful, for example, to identify correlations between visible anatomical tissue structures and haptic feedback imparted by the tissue structure in response to palpation by a robot-assisted instrument. In some embodiments, correlated motion picture image patterns and haptic feedback information are associated with expert surgeon diagnosis evaluations for use in surgeon training.

Minimally Invasive Teleoperated Surgical System

Teleoperation refers to operation of a machine at a distance. In a minimally invasive teleoperation medical system, a surgeon may use an endoscope that includes a camera to view a surgical site within a patient's body. In some embodiments, stereoscopic images can be captured, which allow the perception of depth during a surgical procedure.

Referring now to the drawings, in which like reference numerals represent like parts throughout the several views, FIG. 1 is a plan view of a minimally invasive teleoperated surgical system 10, typically used for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart(s) 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which can be manipulated by the patient-side cart 22 to orient the endoscope 28. Computer processors located on the electronics cart 24 can be used to process the images of the surgical site for subsequent display to the surgeon 18 through the surgeon's console 16. Note that while discrete system components (i.e., patient side cart 22, electronics cart 24, and surgeon's console 16) are depicted and described for exemplary purposes, in various embodiments the elements included therein can be combined and/or separated. For example, in some embodiments, the computer processors of electronics cart 24 can be incorporated into surgeon's console 16 and patient side cart 22. The number of surgical instruments 26 used at one tone will generally depend on the diagnostic or surgical procedure and the space constraints within the operative site among other factors. If it is necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
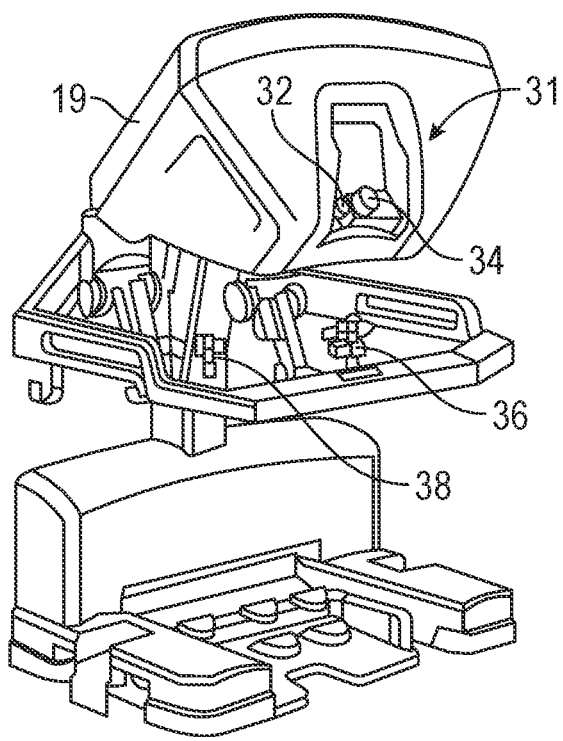
FIG. 2 is a perspective view of a surgeon's console.

FIG. 2 is a perspective view of the surgeon's console 16. The surgeon's console 16 includes a viewer 31 that includes a left eye display 32 and a right eye display 34 for presenting the surgeon 18 with a coordinated stereoscopic view of the surgical site that enables depth perception. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints. Note that while a physical console 16 with a fixed viewer 31 and mechanically coupled control inputs 36 is depicted and described for exemplary purposes, in various other embodiments, "ungrounded" control inputs and/or display structures can be used. For example, in some embodiments, viewer 31 can be a head-mounted display and/or control inputs 36 can be mechanically independent of any base structure (e.g., wired, wireless, or gesture-based, such as Kinect from Microsoft).

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
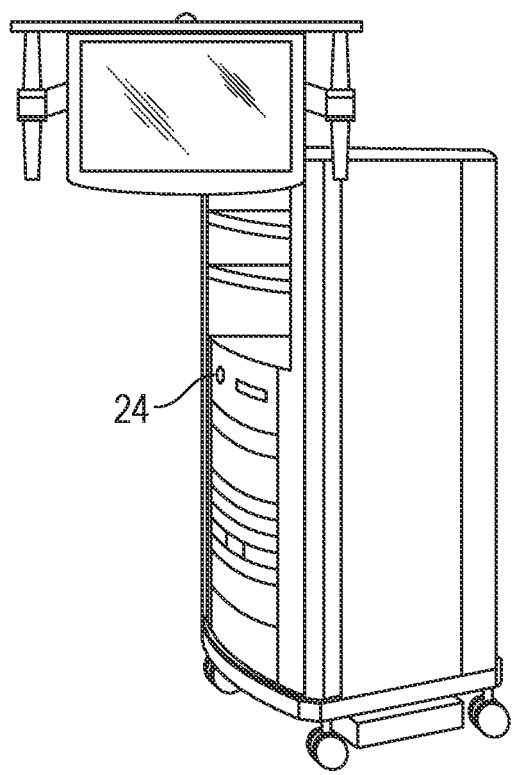
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
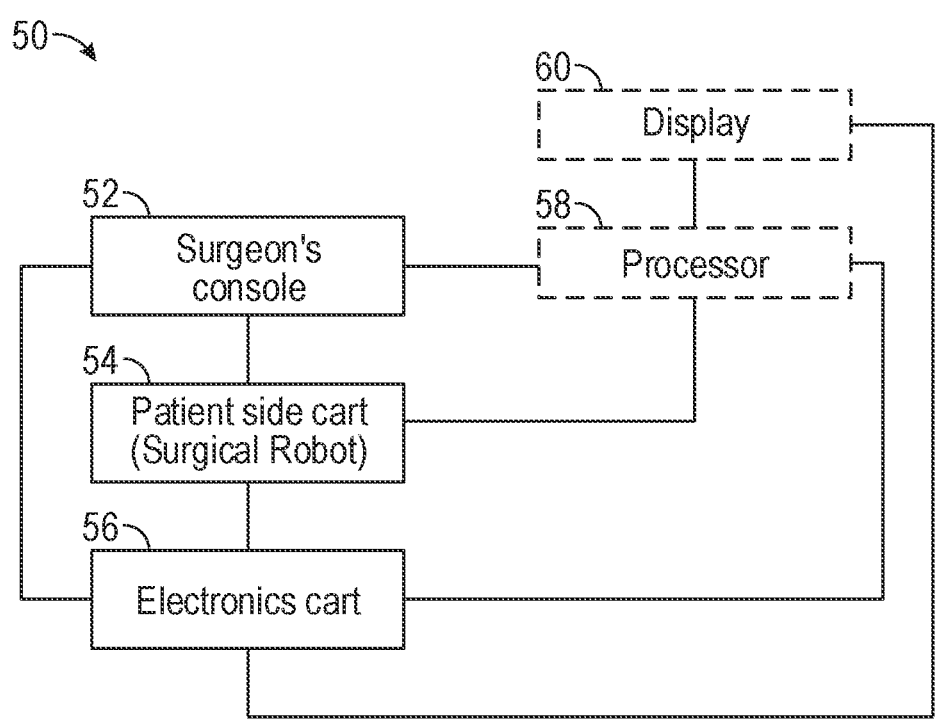
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). A surgeon's console 52 (such as surgeon's console 16 in FIG. 1) can be used by a surgeon to control a patient-side cart 54 (such as patent-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Additionally or in the alternative, the captured images can undergo image processing by a computer processor located outside of electronics cart 56. In one aspect, teleoperated surgical system 50 includes an optional computer processor 58 (as indicated by dashed line) similar to the computer processor located on electronics cart 56, and patient-side cart 54 outputs the captured images to computer processor 58 for image processing prior to display on the surgeon's console 52. In another aspect, captured images first undergo image processing by the computer processor on electronics cart 56 and then undergo additional image processing by computer processor 58 prior to display on the surgeon's console 52. Teleoperated surgical system 50 can include an optional display 60, as indicated by dashed line. Display 60 is coupled with the computer processor located on the electronics cart 56 and with computer processor 58, and captured images processed by these computer processors can be displayed on display 60 in addition to being displayed on a display of the surgeon's console 52.

Figure 5A:
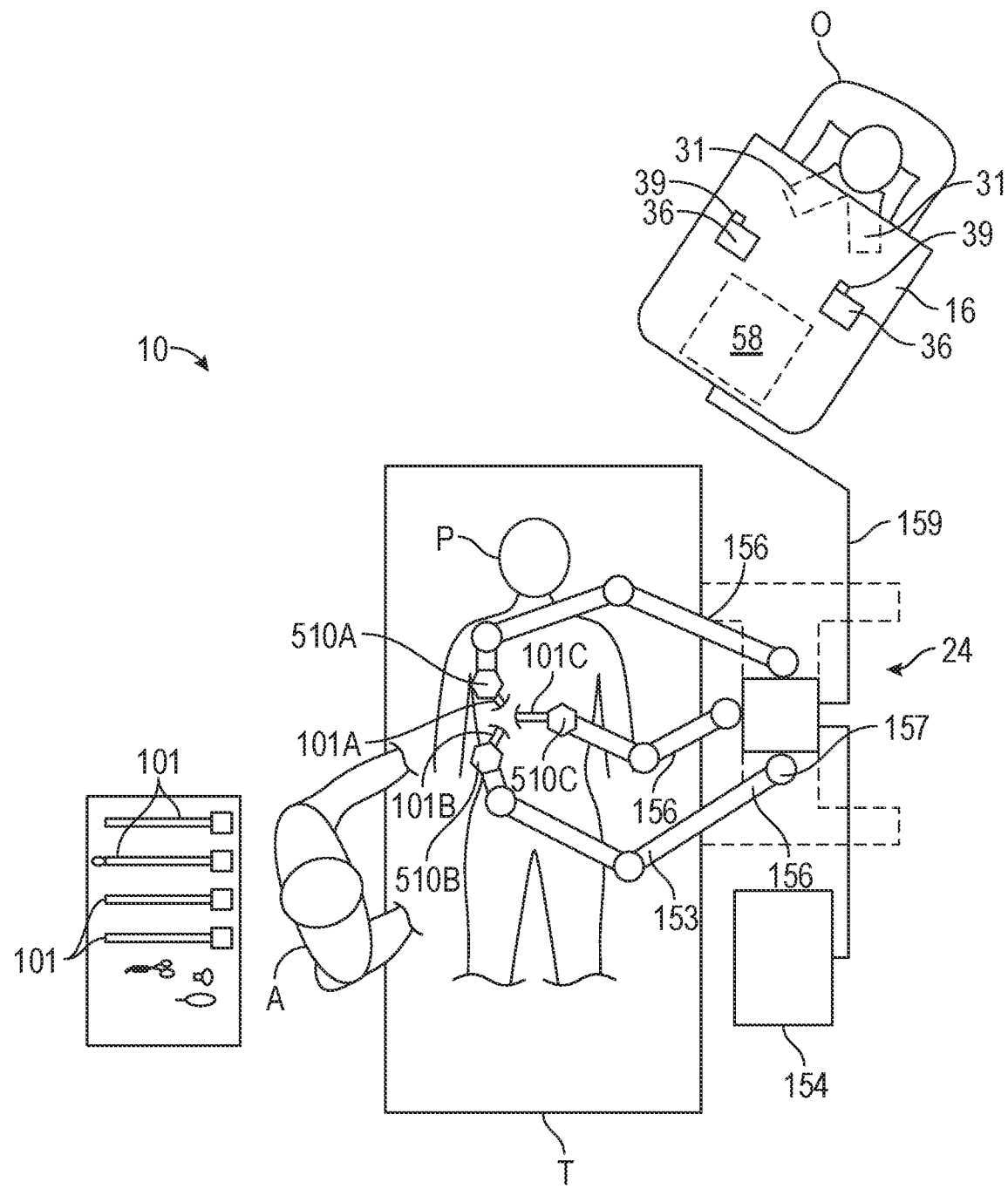
FIG. 5A is an illustrative diagram of the teleoperated surgical system.

FIG. 5A is an illustrative simplified block diagram showing arrangement of components of the teleoperation surgery system 10 to perform surgical procedures using one or more mechanical support arms 510 in accordance with some embodiments. Aspects of system 10 includes robot-assisted and autonomously operating features. These mechanical support arms 510 often support a surgical instrument. For instance, a mechanical surgical arm (e.g., the center mechanical surgical area 510C) may be used to support an endoscope with a stereo or three-dimensional surgical image capture device 101C. The mechanical surgical arm 510C may include a sterile adapter, or a clamp, clip, screw, slot/groove, or other fastener mechanism to mechanically secure an endoscope that includes the image capture device 101C to the mechanical arm.

A user or operator O (generally a surgeon) performs a surgical procedure on patient P by manipulating control input devices 36, such as hand grips and foot pedals at a master control console 16. The operator can view video frames of images of a surgical site inside a patient's body through a stereo display viewer 31. A computer processor 58 of the console 16 directs movement of teleoperationally controlled endoscopic surgical instruments 101A-101C via control lines 159, effecting movement of the instruments using a patient-side system 24 (also referred to as a patient-side cart).

The patient-side system 24 includes one or more mechanical support arms 510. Typically, the patient-side system 24 includes at least three mechanical surgical arms 510A-510C (generally referred to as mechanical surgical support arms 510) supported by corresponding positioning set-up arms 156. The central mechanical surgical arm 510C may support an endoscopic camera 101C suitable for capture of images within a field of view of the camera. The mechanical surgical support arms 510A and 510B to the left and right of center may support instruments 101A and 101B, respectively, which may manipulate tissue.

Figure 5B:
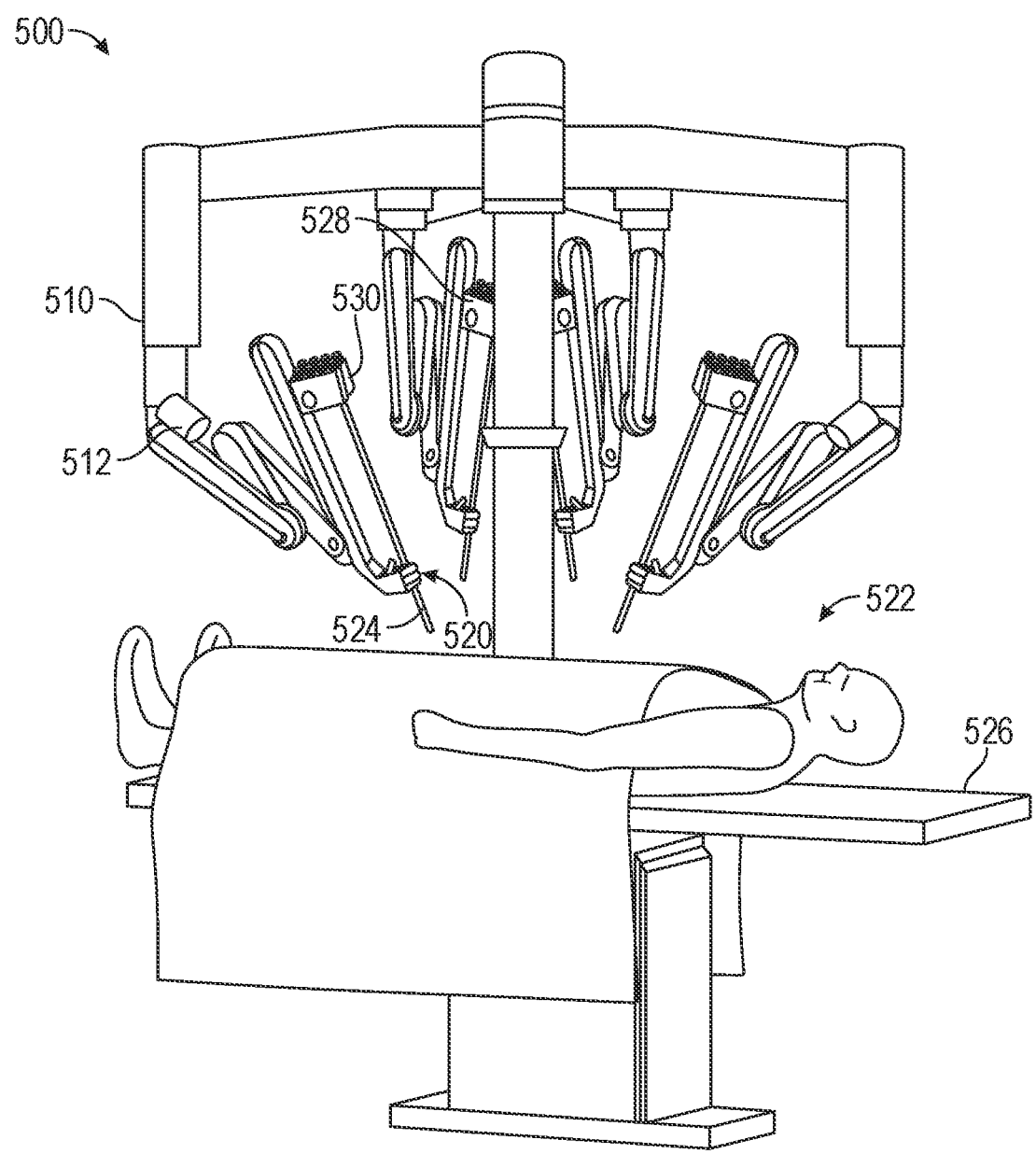
FIG. 5B is a perspective view of a patient-side cart of the surgical system.

FIG. 5B is a perspective view of a patient-side cart 500 of a minimally invasive teleoperated surgical system 10, in accordance with embodiments. The patient-side cart 500 includes one or more support arm assemblies 510. A surgical instrument manipulator 512 is mounted at the end of each support arm assembly 510. Additionally, each support arm assembly 510 can optionally include one or more setup joints (e.g., unpowered and/or lockable) that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while the patient-side cart 500 is shown as including four surgical instrument manipulators 512, more or fewer surgical instrument manipulators 512 may be used.

A functional teleoperated surgical system will generally include a vision system portion that enables a user of the teleoperated surgical system to view the surgical site from outside the patients body 522. The vision system typically includes a camera instrument 528 for capturing video images and one or more video displays for displaying the captured video images. In some surgical system configurations, the camera instrument 528 includes optics that transfer the images from a distal end of the camera instrument 528 to one or more imaging sensors (e.g., CCD or CMOS sensors) outside of the patient's body 522. Alternatively, the imaging sensor(s) can be positioned at the distal end of the camera instrument 528, and the signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, Calif.

Referring to FIGS. 5A-5B, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

In one aspect, surgical instruments 520 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, such as one or more motors to which surgical instrument 520 is coupled. In this manner, the surgical instrument 520 moves in response do a medical person's movements of the control input. In one aspect, one or more control inputs are included in a surgeon's console such as surgeon's console 16 shown at FIG. 2. A surgeon can manipulate control input devices 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIGS. 5A-5B, in one aspect, a surgical instrument 520 and a cannula 524 are removably coupled to manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. In one aspect, the instrument carriage 530 houses one or more teleoperated actuators inside that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In accordance with some embodiments, the surgical system 10 can have multiple system actuation states including docked, following, instrument types and head-in. During a docked system state, one or more manipulator 512 have been coupled to cannula 524. During a following system state, the surgical instrument ("slave") is tracking the control input ("master" command). During an instrument-types system state, the system system has installed in it a set of instruments suitable for performance of a particular surgical procedure or suitable for performance of a particular surgical activity during a surgical procedure. During a head-in system state, the system is waiting for the surgeon to indicate he/she has taken hold of the "master" control input device.

In an alternate embodiment, instrument carriage 530 does not house teleoperated actuators. Teleoperated actuators that enable the variety of movements of the end effector of the surgical instrument 520 are housed in a location remote from the instrument carriage 530, e.g., elsewhere on patient-side cart 500. A cable-based force transmission mechanism or the like is used to transfer the motions of each of the remotely located teleoperated actuators to a corresponding instrument-interfacing actuator output located on instrument carriage 530. In some embodiments, the surgical instrument 520 is mechanically coupled to a first actuator, which controls a first motion of the surgical instrument such as longitudinal (z-axis) rotation. The surgical instrument 520 is mechanically coupled to a second actuator, which controls second motion of the surgical instrument such as two-dimensional (x, y) motion. The surgical instrument 520 is mechanically coupled to a third actuator, which controls third motion of the surgical instrument such as opening and closing or a jaws end effector.

Figure 5C:
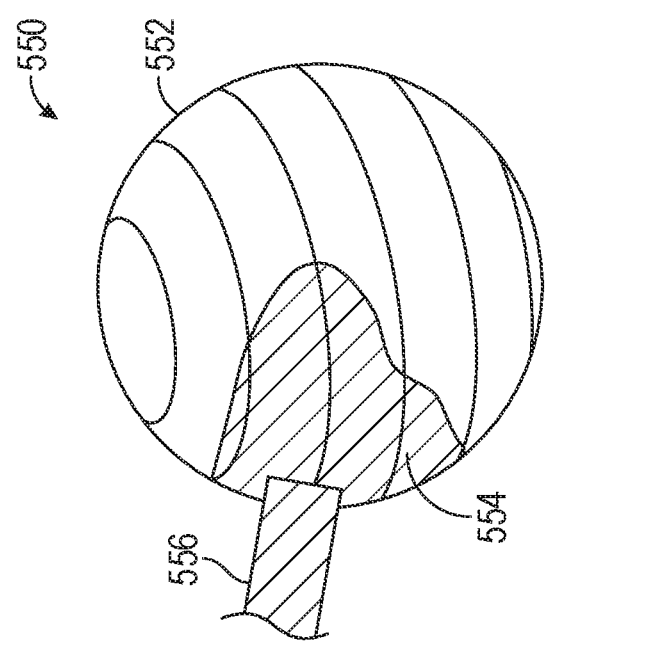
FIG. 5C is an illustrative view of a surgical scene.

FIG. 5C is an illustrative view representing a surgical scene 550 and also showing an endoscope 101C mounting a camera 528 used to record the scene in accordance with some embodiments. The scene 550 is disposed within a patient's body cavity. The scene 550 includes an example hypothetical spherical anatomical structure 552 that includes geometric contours 554. The scene 550 encompasses a surgical instrument 556. A camera 528 mounted on an endoscope 101C captures the scene, which is displayed within the viewer 31 and which is recorded for playback later.

Figure 6:
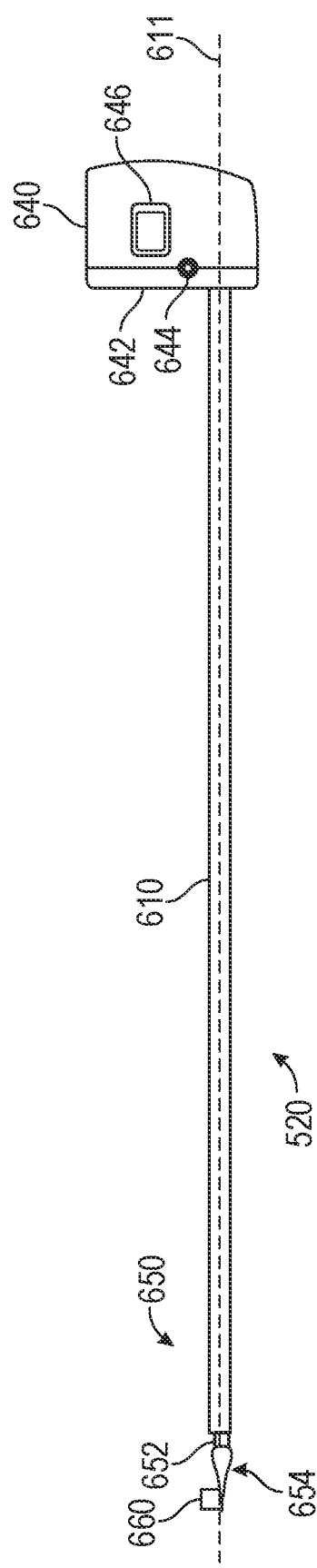
FIG. 6 is an elevation view of a surgical instrument.

FIG. 6 is a side view of a surgical instrument 520, which includes a distal portion 650 and a proximal control mechanism 640 coupled by an elongate tube 610 having an elongate tube centerline axis 611. The surgical instrument 520 is configured to be inserted into a patients body and is used to carry out surgical or diagnostic procedures. The distal portion 650 of the surgical instrument 520 can provide any of a variety of end effectors 654, such as the forceps shown, a needle driver, a cautery device, a cutting tool, an imaging device (e.g., an endoscope ultrasound probe), or the like. The surgical end effector 654 can include a functional mechanical degree of freedom, such as jaws that open or close, or a knife that translates along a path. In the embodiment shown, the end effector 654 is coupled to the elongate tube 610 by a wrist 652 that allows the end effector to be oriented relative to the elongate tube centerline axis 611. Surgical instrument 520 can also contain stored (e.g., on a semiconductor memory associated with the instrument) information, which may be permanent or may be updatable by a surgical system configured to operate the surgical instrument 520. Accordingly, the surgical system may provide for either one-way or two-way information communication between the surgical instrument 520 and one or more components of the surgical system.

Figure 7:
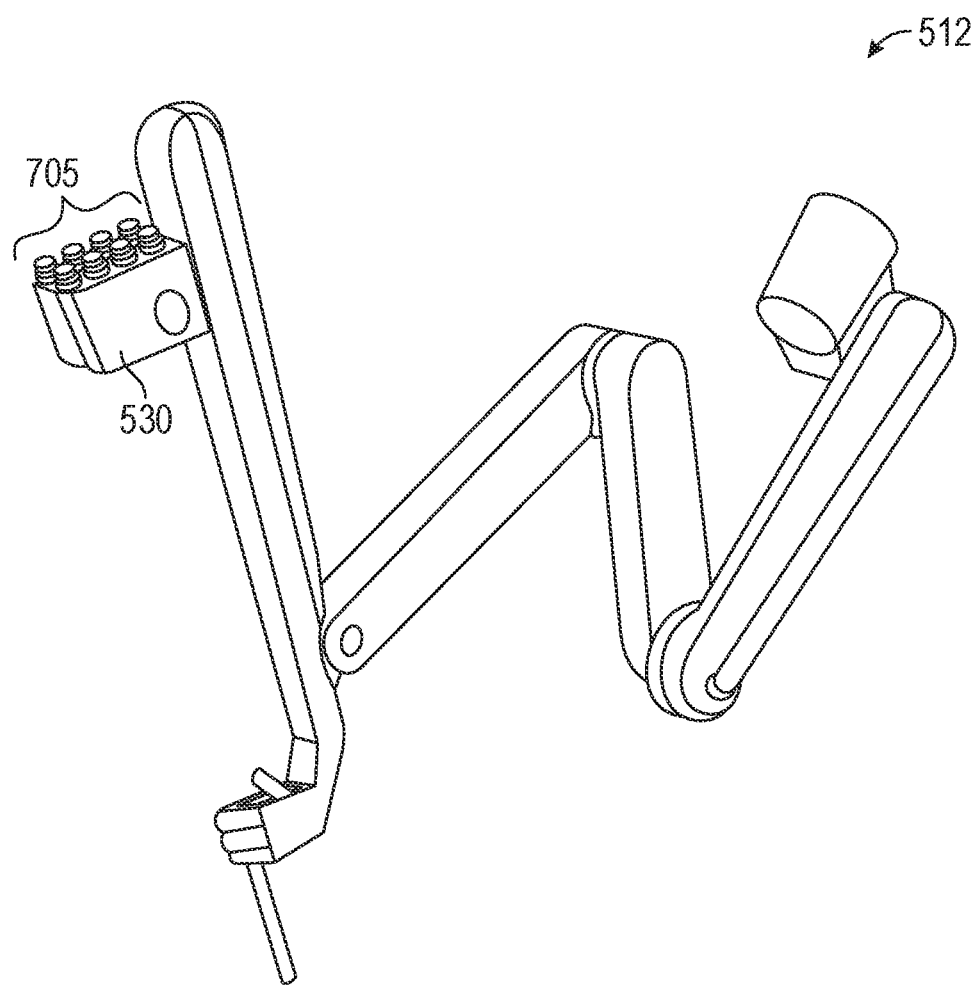
FIG. 7 is a perspective view of an instrument manipulator.

FIG. 7 is a perspective view of surgical instrument manipulator 512. Instrument manipulator 512 is shown with no surgical instrument installed. Instrument manipulator 512 includes an instrument carriage 530 to which a surgical instrument (e.g., surgical instrument 520) can be detachably connected. Instrument carriage 530 houses a plurality of teleoperated actuators. Each teleoperated actuator includes an actuator output 705. When a surgical instrument is installed onto instrument manipulator 512, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs 705 directly contacting corresponding: instrument inputs. In another aspect, this mechanical coupling occurs through an intermediate interface, such as a component of a drape configured to provide a sterile barrier between the instrument manipulator 512 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 512 is surgical instrument 520, shown at FIG. 6. Referring to FIG. 6, in one aspect, movement of one or more instrument inputs of proximal control mechanism 640 by corresponding teleoperated actuators rotates elongate tube 610 and the attached wrist 652 and end effector 654) relative to the proximal control mechanism 640 about elongate the centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.). Accordingly, various mechanical degrees of freedom of a surgical instrument installed onto an instrument manipulator 512 can be moved by operation of the teleoperated actuators of instrument carriage 530.

Annotating a Recorded Video

Figure 8:
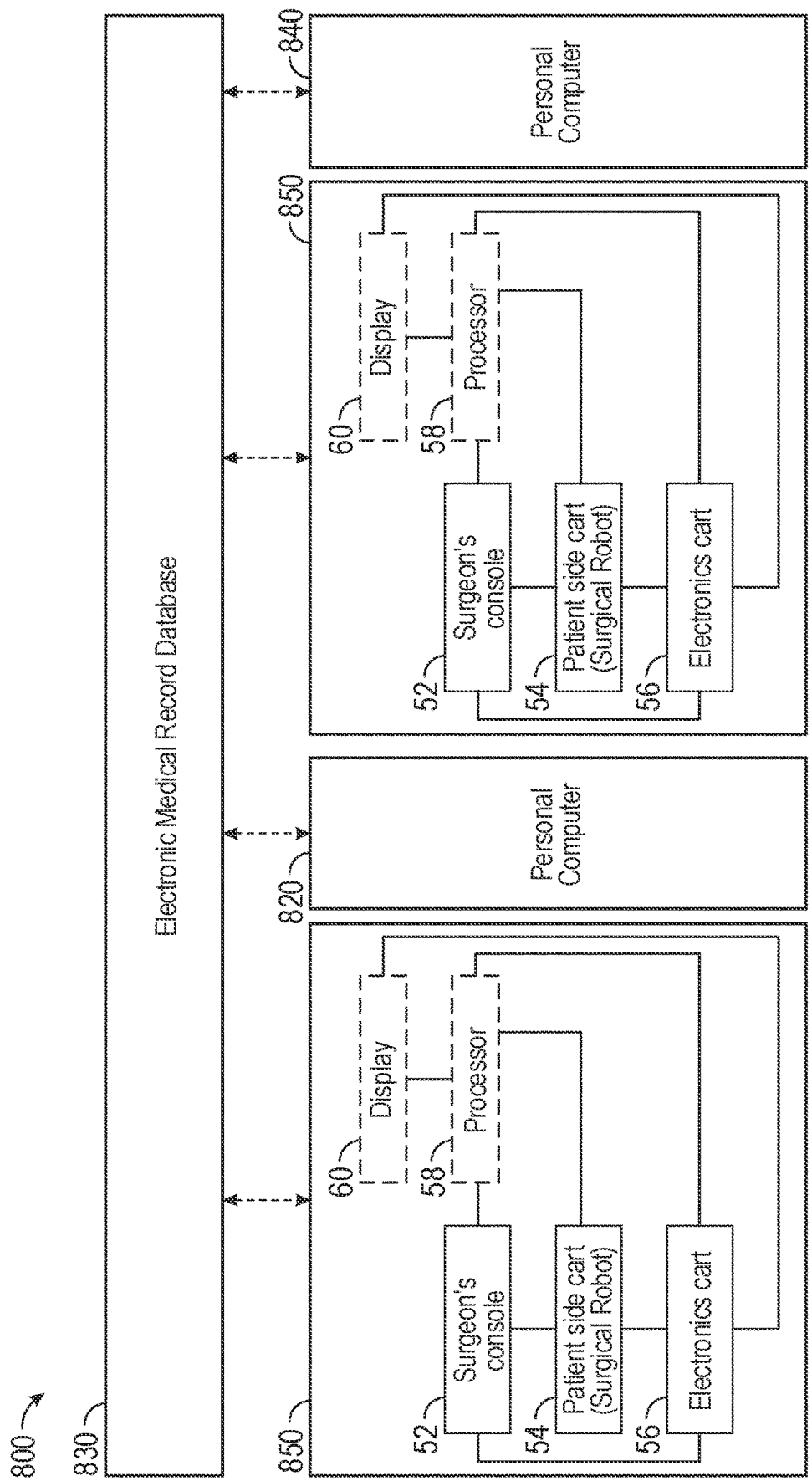
FIG. 8 is a diagrammatic illustration of a surgical planning tool.

FIG. 8 shows a schematic diagram of an exemplary surgical planning tool 800. In one aspect, surgical planning tool 800 includes a teleoperated surgical system 50 in data communication with an electronic medical device record database 830. Teleoperated surgical system 50 shown here is similar to teleoperated surgical system 50 shown at FIG. 4. In one aspect, electronic medical record database 830 includes the medical records of patients that have undergone treatment at a particular hospital or at a plurality of hospitals. Database 830 can be implemented on a server located on-site at the hospital. The medical record entries contained in the database 830 can be accessed from hospital computers through an intranet network. Alternatively, database 830 can be implemented on a remote server located off-site from the hospital, e.g., using one of a number of cloud data storage services. In this case, medical record entries of database 830 are stored on the cloud server, and can be accessed by a computer with internet access.

In one aspect, a surgical procedure is performed on a first patient using teleoperated surgical system 50. An imaging device associated with teleoperated surgical system 50 captures images of the surgical site and displays the captured images as frames of a video on a display of surgeon's console 52. In one aspect, a medical person at surgeon's console 52 highlights or annotates certain patient anatomy shown in the displayed video using an input device of surgeon's console 52. An example of such an input device is control input 36 shown at FIG. 2, which is coupled to a cursor that operates in conjunction with a graphic user interface overlaid onto the displayed video. The graphic user interface can include a QWERTY keyboard, a pointing device such as a mouse and an interactive screen display, a touch-screen display, or other means for data or text entry or voice annotation/or speech to text conversion via a microphone and processor. Accordingly, the medical person can highlight certain tissue of interest in the displayed image or enter a text annotation.

In one aspect, the surgical site video is additionally displayed on a display located on electronics cart 56. In one aspect, the display of electronics cart is a touch-screen user interface usable by a medical person to highlight and annotate certain portions of patient anatomy shown on an image that is displayed for viewing on the display on the electronics cart. A user, by touching portions of patient anatomy displayed on the touch-screen user interface, can highlight portions of the displayed image. Additionally, a graphic interface including a QWERTY keyboard can be overlaid on the displayed image. A user can use the QWERTY keyboard to enter text annotations.

In one aspect, the surgical site video captured by the imaging device associated with teleoperated surgical system 50 is recorded by the teleoperated surgical system 50, and stored on database 830, in addition to being displayed in real time or near real time to a user. Highlights and/or annotations associated with the recorded video that were made by the user can also be stored on database 830. In one aspect, the highlights made by the user are embedded with the recorded video prior to its storage on database 830. At a later time, the recorded video can be retrieved for viewing. In one aspect, a person viewing the recorded video can select whether the highlights are displayed or suppressed from view. Similarly, annotations associated with the recorded video can also be stored on database 830. In one aspect, the annotations made by the user are used to tag the recorded video, and can be used to provide as a means of identifying the subject matter contained in the recorded video. For example, one annotation may describe conditions of a certain disease state. This annotation is used to tag the recorded video. At a later time, a person desiring to view recorded procedures concerning this disease state can locate the video using a key word search.

Retrieval of Stored Video

In some cases, it is desirable for a medical person to be able to view video recordings of past surgical procedures performed on a given patient. In one aspect, a patient who previously underwent a first surgical procedure to treat a medical condition subsequently requires a second surgical procedure to treat recurrence of the same medical condition or to treat anatomy located nearby to the surgical site of the first surgical procedure. In one aspect, the surgical site events of the first surgical procedure were captured in a surgical site video recording, and the video recording was archived in database 830 as part of the patient's electronic medical records. Prior to performing the second surgical procedure on the patient, a medical person can perform a search of database 830 to locate the video recording of the patient's earlier surgical procedure.

In some cases, it is desirable for a medical person planning to perform a surgical procedure on a patient to be able to view video recordings of similar surgical procedures performed on persons having certain characteristics similar to the patient. In one aspect, surgical site video recordings of surgical procedures can be tagged with metadata information such as the patient's age, gender, body mass index, genetic information, type of procedure the patient underwent, etc., before each video recording is archived in database 830. In one aspect, the metadata information used to tag a video recording is automatically retrieved from a patient's then-existing medical records, and then used to tag the video recording before the video recording is archived in database 830. Accordingly, prior to performing a medical procedure on a patient, a medical person can search database 830 for video recordings of similar procedures performed on patients sharing certain characteristics in common with the patient. For example, if the medical person is planning to use teleoperated surgical system 50 to perform a prostatectomy on a 65 year-old male patient with an elevated body mass index, the medical person can search database 830 for surgical site video recordings of prostatectomies performed using teleoperated surgical system 50 on other males of similar age and having similarly elevated body mass index.

In one aspect, a video recording of a surgical procedure is communicated by database 830 to an optional personal computer 820 (as indicated by dashed line), and made available for viewing by a medical person who plans to perform a surgical procedure. Additionally or in the alternative, the video recording of the earlier surgical procedure can be communicated by database 830 to teleoperated surgical system 50, and made available for viewing preoperatively or intraoperatively. In one aspect, the video recording is displayed by teleoperated surgical system 50 on a display located on surgeon's console 52. In another aspect, the video recording of the first surgical procedure is displayed on a display located on electronics cart 56.

Cloud-Based Video Database

In one aspect, database 830 is implemented on a remote server using a cloud data storage service and is accessible by multiple health care providers. Referring to FIG. 8, as shown by dashed line, surgical planning tool 800 optionally includes teleoperated surgical system 850 (as indicated by dashed line) and personal computer 840 (as indicated by dashed line). In one aspect, teleoperated surgical system 850 is similar to teleoperated surgical system 50 and personal computer 840 is similar to personal computer 820, except that teleoperated surgical system 50 and personal computer 820 are located at a first health care provider and teleoperated surgical system 850 and personal computer 840 are located at a second location or even with a second health care provider. In one aspect, a first patient requires surgical treatment of a medical condition, and undergoes a surgical procedure using teleoperated surgical system 50 at the first health care provider. A video recording of the surgical procedure is archived on database 830. At a later time, a second patient requires surgical treatment of the same medical condition, and plans to receive surgical treatment using teleoperated surgical system 850 at the second health care provider. Prior to performing the surgical procedure on the second patient, a medical person accesses database 830 through a secure internet connection and searches database 830 for surgical site video recordings of similar procedures. In one aspect, the medical person treating the second patient is able to retrieve from database 830 the video recording of first patient's surgical procedure, without acquiring knowledge of the identity of the first patient. In this manner, the privacy of the first patient is maintained. In one aspect, the video recording of the first patient's surgical procedure includes highlights and/or annotations made by the medical person who treated the first patient.

Computer Based Pattern Matching and Analysis

Surgical planning tool 800 can includes a pattern matching and analysis algorithm implemented in the form of computer executable code. In one aspect, the pattern matching and analysis algorithm is stored in a non-volatile memory device of surgical planning tool 800, and is configured to analyze the video recordings archived in database 830. As discussed previously, each of the video recordings archived in database 830 can be tagged and/or embedded with certain metadata information. This metadata information can include patient information such as patient age, gender, and other information describing the patient's health or medical history. Additionally, as discussed previously, the metadata information can include highlights or annotations made by a medical person. In one aspect, these highlights and annotations are embedded with the video recording and archived together with the video in database 830.

In one aspect, pattern matching and analysis algorithm includes an image analysis component that identifies patterns in shapes and colors that are shared amongst multiple video recordings stored on database 830. The pattern matching and analysis algorithm then reviews the tagged metadata associated with this subset of video recordings to determine whether any words or phrases are frequently associated with videos within this subset. These analyses performed by pattern matching and analysis algorithm can be used to assist medical persons in making determinations about patient anatomy, preferred surgical approaches, disease states, potential complications, etc.

A Method of Using a Surgical Planning Tool

Figure 9:
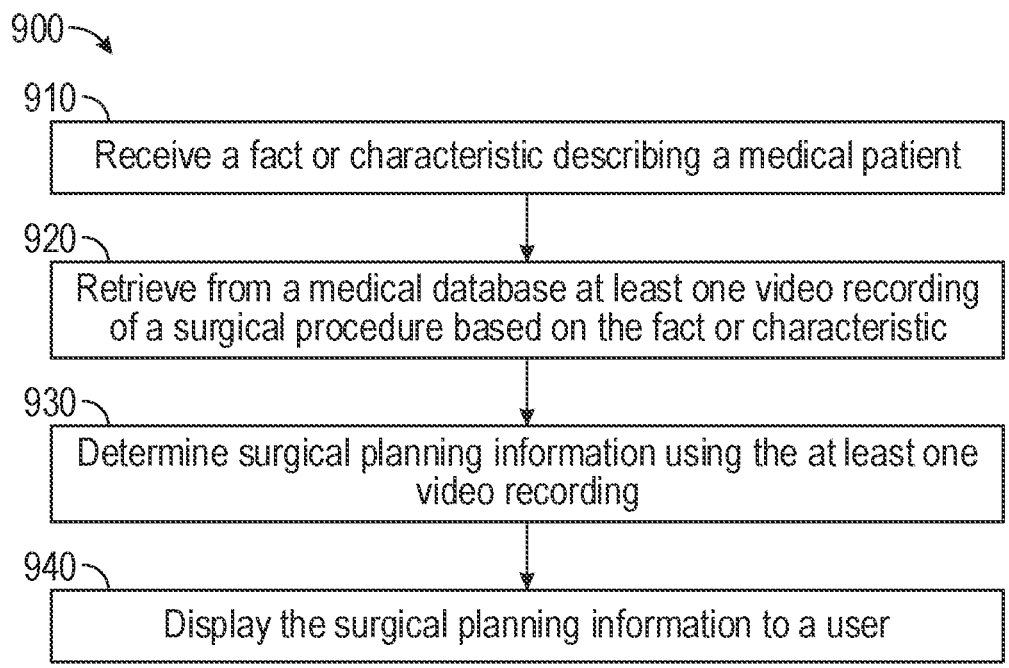
FIG. 9 is a flow diagram of a method of using a surgical planning tool.

FIG. 9 shows a method 900 of using a surgical planning tool. In one aspect, the surgical planning tool is similar to surgical planning tool 800 at FIG. 8. At 910, a fact or characteristic describing a medical patient, e.g., a medical condition suffered by a patient, is received by a medical device. The medical device can receive this fact or circumstance via a user interface located on a teleoperated surgical system (e.g., teleoperated surgical system 10 at FIG. 1 or teleoperated surgical system 50 at FIG. 4), or alternatively, through a personal computer similar to personal computer 820 at FIG. 8. At 920, the medical device uses the fact or characteristic received at 910 to retrieve at least one relevant video recording of a surgical procedure from a medical device database. At 930, the medical device uses the video recordings to determine surgical planning information. In one aspect, the surgical planning information includes the types of instruments used in the recorded procedure. At 940, the medical device displays to a user the surgical planning information determined at 930.

Figure 10:
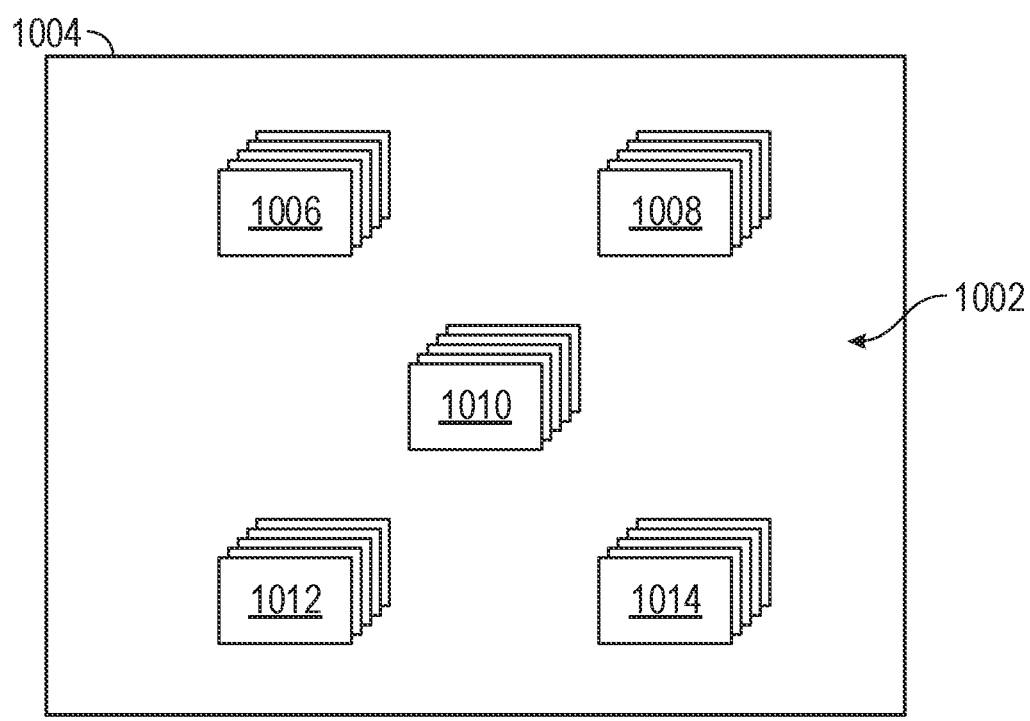
FIG. 10 is an illustrative drawing representing storage atlas in a computer readable storage device in accordance with some embodiments.

FIG. 10 is an illustrative drawing representing storage atlas 1002 in a computer readable storage device 1004 in accordance with some embodiments. The storage atlas 1002 includes first data information structures 1006 that indicate instances of previously performed surgical procedures. Each different instance of a first data information structures 1006 corresponds to a different surgery. Second data information structures 1008, associated with individual surgical events, associate motion picture image segments ($MPI_1$, $MPI_2$, ... $MPI_n$) with kinematic information segments ($KIN_1$, $KIN_2$, ... $KIN_n$), with surgical system actuation states ($Astate_1$, $Astate_2$, ... $Astate_n$) and with corresponding annotations ($ANOT_1$, $ANOT_2$, ... $ANOT_n$) at corresponding time intervals ($t_1$, $t_2$, ... $t_n$). First control signal rules information structure 1010, produced based upon a plurality of surgical events of a given type, associates kinematic/image signature/actuation state combinations with control signals e. g., ($SigK_1 SigI_1$, $Astate_1$, $CNTL_{KIA1}$) ... ($SigK_n$, $SigI_n$, $Astate_n$, $CNTL_{KIAn}$). Each different instance of the first rules information structure 1010 corresponds to a different category of surgery. Third data information structures 1012, associated with individual surgical events, associate motion picture image segments ($MPI_1$, $MPI_2$, ... $MPI_n$) with haptics information segments ($HAP_1$, $HAP_2$, ... $HAP_n$) at corresponding time intervals ($t_1$, $t_2$, ... $t_n$). Second diagnosis rules information structures 1014, produced based upon a plurality of surgical events of a given type, associate diagnosis image signatures ($SigI_{DIAG1}$, $SigI_{DIAG2}$, ... $SigI_{DIAGm}$) with diagnostic kinematic signatures ($SigI_{DIAG1}$, $SigI_{DIAG2}$, ... $SigI_{DIAGm}$) and with diagnoses ($DIAG_1$, $DIAG_2$, ... $DIAG_m$). Each different instance of the second diagnosis rules information structure 1014 corresponds to a different category of surgery.

In accordance with some embodiments, image information can be in the form of video images across the full visual spectrum, fluorescence, hyperspectral, CT/MRI. Image information or a combination of some of these image information can be used as a basis to evaluate disease state/determine diagnosis.

FIG. 11 is an illustrative drawing representing an example instance of a first data information structure 1006 included within the atlas 1002 in the storage device 1004, which includes information about an individual surgical procedure in accordance with some embodiments. It will be appreciated that a multiplicity of surgical procedures are performed on a multiplicity of different patients by many different surgeons using many different instances of a robot-assisted surgical system described herein. An instance of the first data information structure 1006 can be produced and stored in a computer readable storage device for each surgical procedure that is performed. The example first data information structure 1006 includes a surgery type field 1006-1 that indicates the type of surgical procedure, such as prostectomy, hysterectomy, or, partial-nephrectomy, for example.

The example first data information structure 1006 includes a patient health record field 1006-2 that provides information about the patient who is operated upon such as age, body mass, blood type, height, sex, and race, for example. The example first data information structure 1006 includes a physician information field 1006-3 that provides information about the surgeon performs the individual operation such as level of experience in general and level of experience operating a robot-assisted surgical system, for example. The example first data information structure 1006 includes a surgical system field 1006-4 that provides information about the surgical system used to perform the operation such as make, model and serial number, for example. The example first data information structure 1006 includes a surgical recording field 1006-5 that provides information such as motion picture images, instrument kinematics and haptic feedback provided using the system during the surgical procedure. The example first data information structure 1006 includes a surgical recording field 1006-6 that provides annotation information, such as tags containing descriptive information that have been associated with image information, kinetics information or haptics information within the example first data information structure 1006.

FIG. 12 is an illustrative drawing representing an example instance of the second data information structure 1008 included within the atlas 1002 in the storage device 1004, which associates recorded motion picture image segments from an individual surgical procedure, corresponding surgical instrument kinematics information segments, corresponding surgical system actuation states, and corresponding annotations, in accordance with some embodiments. The example second data information structure 1008 provides additional details of information within the recording field 1006-5 of the first data information structure 1006. In one aspect, motion picture images of patient anatomy structures, corresponding surgical instrument kinematics, and corresponding surgical system actuation states, are recorded and time stamped (t1, t2 ... tn) during a surgery to produce a chronological record of surgical activities and corresponding surgical instrument kinematics during the surgical procedure. In some embodiments, the motion picture images also encompass images of surgical instruments used to operate upon the anatomical structures during a surgery. Time stamps temporally align motion picture images with surgical instrument kinematics.

During a surgery, a user such as a surgeon or another member of a surgical team, may annotate recorded motion picture information and associated recorded surgical instrument kinematics information with metadata that indicate corresponding surgical activity such as dissection or suturing, anatomical features, particular surgical complexities, surgeon observations, or phase of the procedure, for example. The annotations may include one or more of or a combination of written notes tagged to recorded motion picture information and/or recorded surgical instrument kinematics information, coloring or highlighting (e.g., telestration) of images in the video recordings, for example. The annotations may be added later to a time stamped recorded image information and/or recorded kinematic information, for example.

It will be appreciated that during a teleoperated surgical procedure, a surgical activity can occur that results in a change in surgical system actuation state. A surgeon may move his head into and out of the viewer 31 resulting in a change in head-in state. A surgeon may move his hands or feet in and out of contact with control inputs 36 resulting in a change in following state, for example. A combination of instruments in use may be changed, resulting in a change in instruments type state, for example.

Operation of the surgical instrument in support of the surgical activity in the one or more surgical states results in generation of kinematic information within a surgical system that indicates instrument motion, which is indicative of the actual manner in which a surgeon performed the surgical activity. A surgeon may have moved an instrument rapidly or slowly, for example. A surgeon may have moved a surgical instrument in a direction toward or in a direction away from an anatomical structure along one or another path, for example. A surgeon, before actuating a particular instrument, may have adjusted a position of a different instrument, for example. It will be appreciated that a combination of recorded anatomical structure image information and recorded instrument kinematic information, and recorded system actuation state provides a record of what images were presented to a surgeon during a surgery and what activities the surgeon engaged in in concert with those images and what the system actuation state of the surgical system was at the time. Corresponding annotations can provide additional insight into associated images and kinematics recorded in the course of a surgical procedure. Note that wade kinematic information can be derived directly from the surgical system (e.g., via joint data or other mechanical tracking), in various other embodiments, kinematic information can be extracted from image processing or sensor data (e.g., tool/instrument tracking within the endoscope image).

FIGS. 13A-13C are illustrative drawings showing an example surgical instrument 1202 and an actuator assembly 1203 in which the surgical instrument is shown in three different example surgical instrument actuation states in accordance with some embodiments. The example instrument 1202 includes a jaw end effector 1204 that can transition between open and closed states and a continuum of partially opened/partially closed states in between. The example instrument 1202 also includes a two degree of freedom (2-dof) wrist 1206 that can move between different two-dimensional (x, y) positional states. The example actuator assembly 1203 includes a first actuator 1208, which in some embodiments includes a jaw motor (JM) used to actuate the jaw end effector 1204. The example actuator assembly 1203 includes a second actuator 1210, which in some embodiments includes a wrist motor (WM) used to actuate the wrist 1206. During a surgery, the surgical instrument 1202 may transition through multiple instrument actuation states corresponding to different activities during a surgical procedure. Each transition results in generation of kinematics information that is captured and stored and that is indicative of motion of the instrument as it transitions from its physical location and disposition (e.g., open or closed) in one state to its physical location and disposition in a next state. As represented in FIG. 13A, for example, a surgical procedure may involve a first surgical activity in which the first actuator 1208 (the JM) disposes the jaw end effector 1204 to a frilly open state and the second actuator 1210 the (WM) disposes the wrist 1206 to a first positional state (x1, y1). As represented in FIG. 13B, for example, the surgical procedure may involve a second surgical activity in which the first actuator 1208 transitions the jaw end effector 1204 to a fully closed state and the second actuator 1210 transitions the wrist 1206 to a second positional state (x2, y2). As represented in FIG. 13C, for example, the surgical procedure may involve a third surgical activity in which the first actuator 1208 disposes the jaw end effector 1104 in a partially open/partially closed state and the second actuator 1210 transitions the wrist 1206 to a third positional state (x3, y3).

Figure 14:
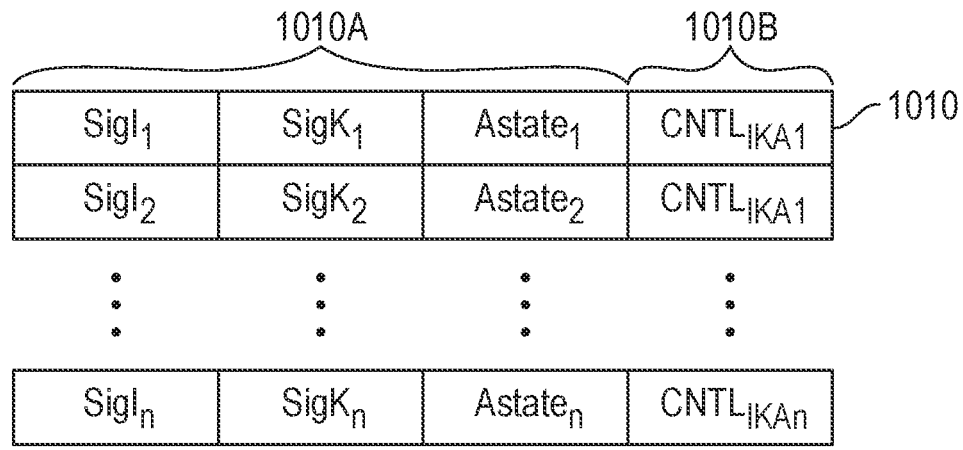
FIG. 14 is an illustrative drawing representing an example instance of control signal rules information structure, which includes rules to associate kinematics, images and system actuation states with control signals in accordance with some embodiments.

FIG. 14 is an illustrative drawing representing an example instance of the first control signal rules information structure 1010 included within the atlas 1002 in the storage device 1004, which includes rules to associate kinematic signature information, image signature information, and system actuation state information with control signals, in accordance with some embodiments. The rules are developed based upon data from prior surgeries represented in the first and second data information structures 1006, 1008. The first rules correlate patterns of anatomical images, instrument kinematics and system state with control signals used to control operation of the system or to p guidance to a surgeon during a surgical procedure.

In accordance with some embodiments, a kinematic signature includes a multi dimensional vector. In some embodiments, recorded kinematic motion of an instrument is decomposed into multiple vectors representing kinematic features such as instantaneous velocity, instantaneous acceleration, instantaneous three-dimensional positon, current path of motion and predicted path of motion, for example. Not only can the motion and position of an instrument, but also its context such as physical location of an anatomical structure relative to the instrument, physical location of other instruments, a patient's health and the nature of a surgery be relevant to interpretation of an kinematic information. Moreover, previous instrument motions can be relevant to an evaluation, such as where to move an instrument next, that is to be based at least in part upon instrument kinematics. Thus, in some embodiments, an instrument kinematics vector also includes vectors indicative of location of anatomical structures, location of other instruments, patient health, type of surgery and prior motion of an instrument, for example.

In accordance with some embodiments, an image signature includes a multi-dimensional vector. In some embodiments, recorded motion picture images of an anatomical structure are decomposed into multiple vectors representing image features such as color, texture and geometry, for example. Moreover, in a convolutional neural network, there are lower-level features (e.g., color edges, etc.); in subsequent layers, higher level features are learned, ultimately resulting in e.g., a classification of the anatomical structure or tissue type. Not only can the appearance of an anatomical structure, but also its context such as patient's health, the nature of a surgery, a surgeon's skill level at the particular type of robot assisted surgery, and whether or not system state indicates that the correct surgical instruments currently are installed in the system, be relevant to interpretation of an anatomical image. Moreover, changes in appearance of an anatomical stricture in the course of a surgical procedure can be relevant to interpretation of an anatomical image. Thus, in some embodiments, an image vector also includes vectors indicative of patient health record information, surgery type, and comparison of anatomical image appearance at different surgical stages, for example.

In accordance with some embodiments, different control signals are associated with different combinations of image signatures, kinematics signatures and actuation system state. In some embodiments, some control signals control instrument actuation state. For example, some combination of image signature, kinematics signature and actuation system state may correspond to an unsafe surgical activity, and a corresponding control signal may operate to cause a surgical system to freeze motion of an instrument and/or generate a notification to a surgeon (e.g., a visible, audible, and/or tactile warning, or an indication that related guidance/information is available), For example, instrument motion outside the field of view of the camera. Alternatively, for example, some combination of image signature, kinematics signature and actuation system state may correspond to an especially delicate surgical activity, and a corresponding control signal may operate to cause a surgical system to slow rate of motion of an instrument to a safer speed or may limit a range of motion of an instrument to avoid injury or may generate a recommendation notification to a surgeon (e.g., overlay of corrective/warning information displayed within a viewer or presentation of access to related guidance/information). For example, preservation of nerves during prostatectomy, or suturing during mitral valve repair.

In accordance with some embodiments, machine learning techniques can be used to generate image signatures and to generate kinematics signatures. More specifically, for example, classifiers can be used together with expert knowledge to correlate image signatures and kinematics signatures with control signals. Surgical data within the first and second data information structures 1006, 1008 are evaluated, based upon expert surgeon input for example, to determine appropriate system operation in context of different anatomical images, instrument kinetics and surgical system state. Control signals to effect the determined system operation are associated in the first rules information structure 1010 with anatomical image signatures, instrument kinematics signatures and system states. In accordance with some embodiments, image signatures and kinematics signatures can be combined together with system state information to produce one overall signature that corresponds to a control signal.

Figure 15:
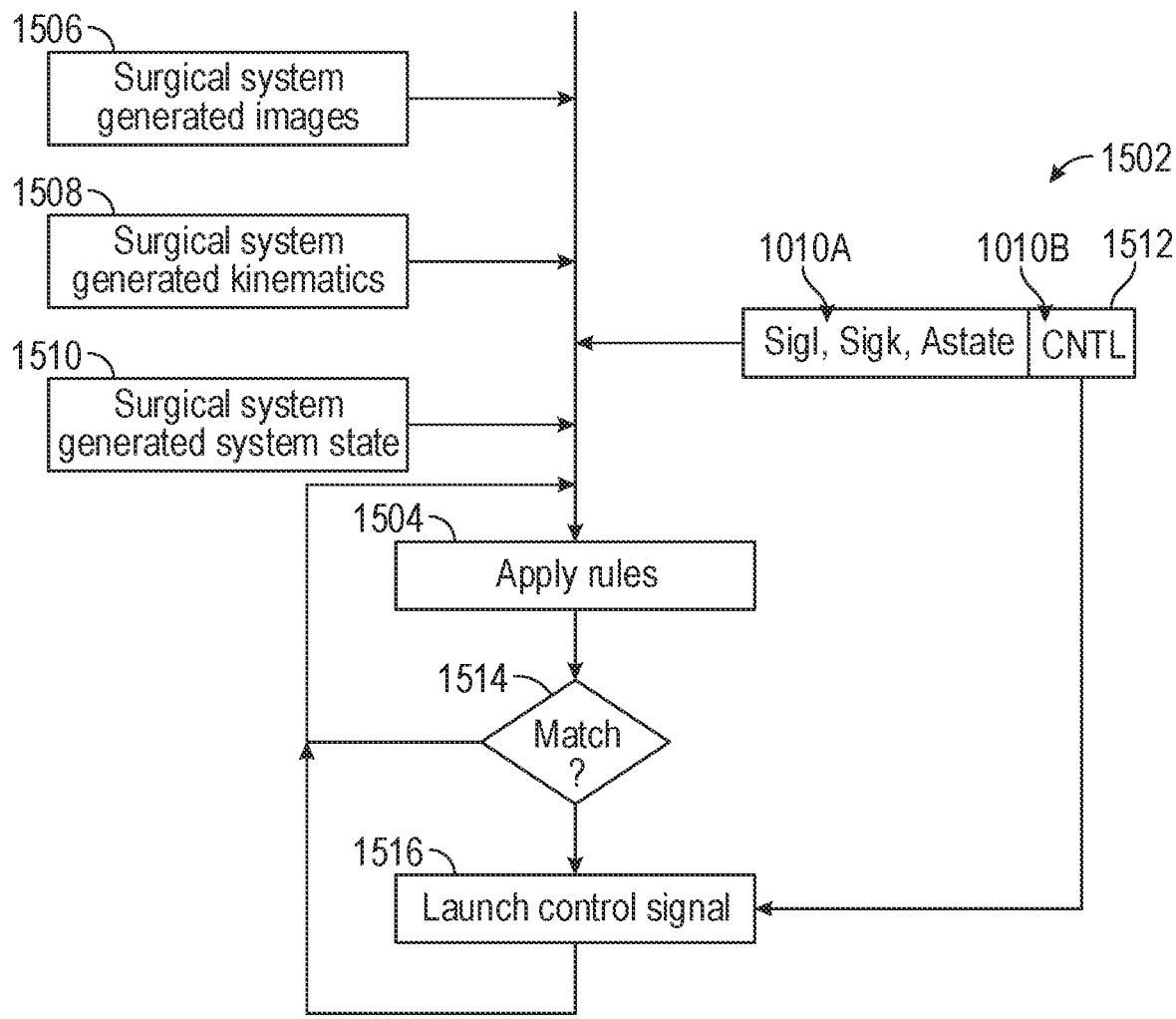
FIG. 15 is an illustrative flow diagram representing a process to produce a control signal based at least in part upon anatomical image information, instrument kinematics and system state, in accordance with some embodiments.

FIG. 15 is an illustrative flow diagram representing a process 1502 to produce a control signal based at least in part upon anatomical image information, instrument kinematics and system state, in accordance with some embodiments. The computer processor 58 is configured to perform the process 1502 in accordance with some embodiments. During performance of a surgical procedure, a rules block 1504 determines whether to cause a launch of a control signal based upon motion picture images, instrument kinematics and surgical system state system state during the surgery, and rules from the first rules information structure 1010.

More particularly, during performance of a surgical procedure using system 10, rules block 1504 receives motion picture image information generated during the surgery, receives instrument kinematics information generated during the surgery and receives system state information generated during the surgery. The camera 528 captures motion picture information during the surgery. The computer processor 58 at block 1506, provides corresponding image information to the rules block 1504. Instrument actuators, such as actuators 1208, 1210, receive actuation commands that result in instrument motion during a surgery. The computer processor 58 at block 1508, determines instrument kinematic information based upon the actuation commands and provides the kinematic information to the rules block 1504. The system includes sensors (not shown) that sense system state, such as whether an operator has his head placed against the viewer, whether the operator has engaged control inputs with hands and/or feet 36, and which instruments are inserted for use. The computer processor 58 at block 1510, provides the system state information to the rules block 1504.

Also, during the surgical procedure, a control signal rules storage block 1512 provides to the rules block 1504, image signature information, kinematics signature information, and system actuation state information from within a first rules block portion 1010A of the first control signal rules information structure 1010. The rules block 1504 compares image, kinematics and system information provided by blocks 1506, 1508, 1510, respectively, with associated image signature (SigI), kinematics signature (SigK) and system state (Astate) information from the first rules block portion 1010A. It will be appreciated that in some embodiments, the computer processor 58 is configured to transform image, kinematics and system information generated by the system 10 into a format suitable for comparing against signature and state information from the first portion 1010A of the control signal rules information structure 1010. In particular, in some embodiments raw image/kinematics/system state is processed to derive a classification (signal/probability) which then is looked up in a table to determine what action to take based upon a determined classification.

Decision module 1506 determines whether a match occurs between the provided image, kinematics and system state information and rules information from the first rules block portion 1010A. It will be appreciated that in machine learning embodiments a match is determined based upon a range of similarity between the image, kinematics and system state information and rules information. Thus, for example, a combination of generated image, generated kinematics and generated system state information that is within some threshold limit of a certain rule is determined to match that rule.

Block 1514, in response to determination of a match between a combination of image, kinematics and system state information and a rule, launches a control signal from within a second rules portion 1010B of the control signal rules information structure 1010 that corresponds the matching rule. For example, in response to determination that image, kinematics and system state information received during a surgical procedure matches $SigI_2$, $SigK_2$ and $Astate_2$ of the first portion 1010A, block 1516 launches signal $CNTL_{IKA2}$ from within a second portion 101B of the control signal information structure 1010. Thus, the launched control signal depends upon actual system information. Moreover, a launched control signal can be operative to control instrument actuation. A control signal can be launched that prevents certain instrument motion, such as to avoid collision with another instrument, for example. A control signal can be launched that controls how certain instrument motion occurs, such as by limiting rate of speed, for example. A control signal can be launched that controls what an instrument does next such as moving an instrument to a neutral position to prevent a collision with an instrument that a surgeon is likely to use next, for example. While no match is detected, decision module feeds back control flow to the rules block 1504. Similarly, after the launch of a control signal, control flows back to the rules block 1504 to continue with comparisons of image, kinematics and system information generated during a surgery with rules from the control signal information structure 1010.

Figures 16, 17:
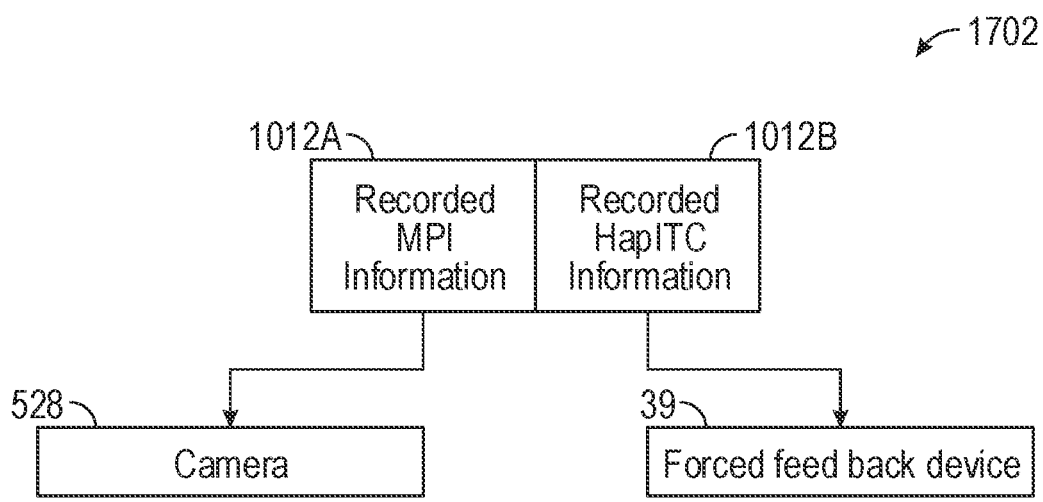
FIG. 16 is an illustrative drawing representing an example instance of the third data information structure included within the atlas, which associates recorded motion picture image segments with haptics information segments, in accordance with some embodiments.
FIG. 17 is an illustrative flow diagram representing a process to configure a teleoperated robot-assisted surgical system to playback a surgical experience, in accordance with some embodiments.

FIG. 16 is an illustrative drawing representing an example instance of the third data information structure 1012 included within the atlas 1002 in the storage device 1004, which associates recorded motion picture image segments with haptics information segments, in accordance with some embodiments. The example third data information structure 1012 provides additional details of information within the recording field 1006-5 of the first data information structure 1006. In one aspect, motion picture images of patient anatomy structures and corresponding haptic feedback information imparted to a surgeon/operator are recorded and time stamped (t1, t2 . . . tn) during a surgery to produce a chronological record of what a surgeon observed and what a surgeon sensed through a physical touch sensation at the control input during the surgical procedure. Time stamps temporally align motion picture images with surgical instrument kinetics.

Haptics generally describes touch feedback, which may include kinesthetic (force) and cutaneous (tactile) feedback, as well as vibration and movement. In teleoperation surgery systems, natural haptic feedback is largely eliminated because a surgeon does not manipulate an instrument directly. Referring to FIG. 6, in accordance some embodiments, an artificial haptic sensor 660 mounted on a patient-side of a surgical instrument 520 can acquire haptic information, and haptic displays on the surgeon side to convey the sensed information to the surgeon. Referring to FIG. 5A, Kinesthetic or force feedback systems typically measure or estimate the forces applied to patient anatomy within a surgical scene by the surgical instrument, and provide resolved forces to a surgeon's hand via a force feedback device 39 mounted on a control input 36. Tactile feedback can be used to provide information such as local tissue deformation and pressure the distribution across a tissue surface.

Referring again to FIG. 16, third data information structure 1012 associates motion picture information segments with contemporaneously haptic feedback information delivered to force feedback device 39. As such, the data in the third information structure can represent a record of a surgeon's visual and tactile input during a surgical procedure. This information can be used to aid in training a surgeon in mechanical technique and also as an aid in training a surgeon in diagnosis.

FIG. 17 is an illustrative flow diagram representing a process 1702 to configure a teleoperated robot-assisted surgical system to playback a surgical experience, in accordance with some embodiments. The computer processor 58 is configured to perform the process 1702 in accordance with some embodiments. The processor 58 uses the recorded motion picture information to configure the camera 528 to replay the recorded motion pictures at the viewer. The processor 58 uses the recorded haptic information to configure the force feedback device 39 to impart the recorded haptic feedback at the control input 36. In some embodiments, the force feedback device 39 includes a vibrotactile device.

Figure 18:
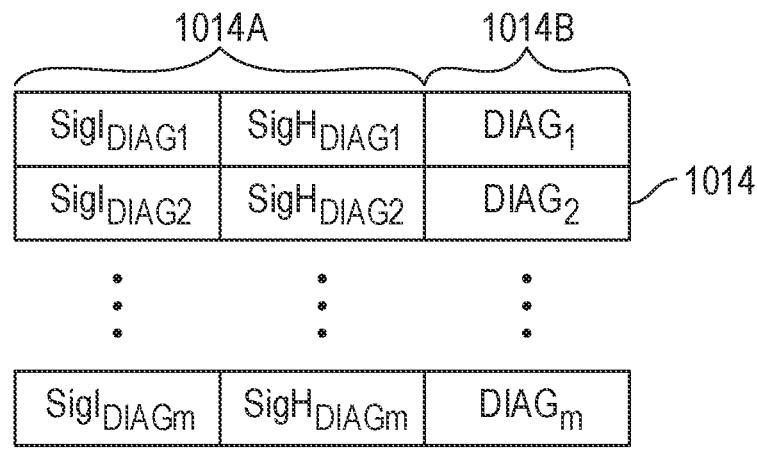
FIG. 18 is an illustrative drawing representing an example instance of the diagnosis rules information structure included within the atlas, which includes rules to associate image signature information and haptic feedback information with diagnoses, in accordance with some embodiments.

It will be appreciated that such replay can be helpful in training a surgeon to more effectively use a surgical system based upon that surgeon's own prior surgical experience or based upon that of another. By looking into the viewer 31 and touching the control input 36 while the images and corresponding haptic feedback forces are replayed, a surgeon can experience a recorded surgery. A surgeon then can experiment with alternate surgical approaches and compare the visual and tactile sensations during those alternate approaches with those of a prior surgery, for example. FIG. 18 is an illustrative drawing representing an example instance of the second diagnosis rules information structure 1014 included within the atlas 1002 in the storage device 1004, which includes rales to associate image signature information and haptic feedback information with diagnoses, in accordance with some embodiments. The rules are developed based upon data from prior surgeries represented in the first and third data information structures 1006, 1012. The second rules correlate patterns of anatomical images and haptic feedback with diagnoses.

As explained above, an image signature includes a multi-dimensional vector. Additionally, in accordance with some embodiments, a haptic feedback signature includes a multidimensional vector. In some embodiments, recorded haptic feedback is decomposed into multiple vectors representing haptic feedback features such as location, frequency and intensity of feedback forces. Not only can the location, frequency and intensity of feedback forces, but also its context such as, a patient's health and the nature of a surgery be relevant to interpretation of a feedback signal. Thus, in some embodiments, a multi-dimensional haptic feedback vector also includes vectors indicative of patient health and type of surgery for example.

In accordance with some embodiments, machine learning techniques can be used to generate image signatures and to generate haptic feedback signatures. More specifically, for example, classifiers can be used together with expert knowledge to correlate image signatures and haptic signatures with diagnoses. Surgical data within the first and third data information structures 1006, 1012 are evaluated, based upon expert surgeon input for example, to determine appropriate diagnoses in context of different anatomical images, and haptic feedback forces. In accordance with some embodiments, image signatures and haptics signatures can be combined together produce one overall signature that corresponds to a diagnosis.

Figure 19:
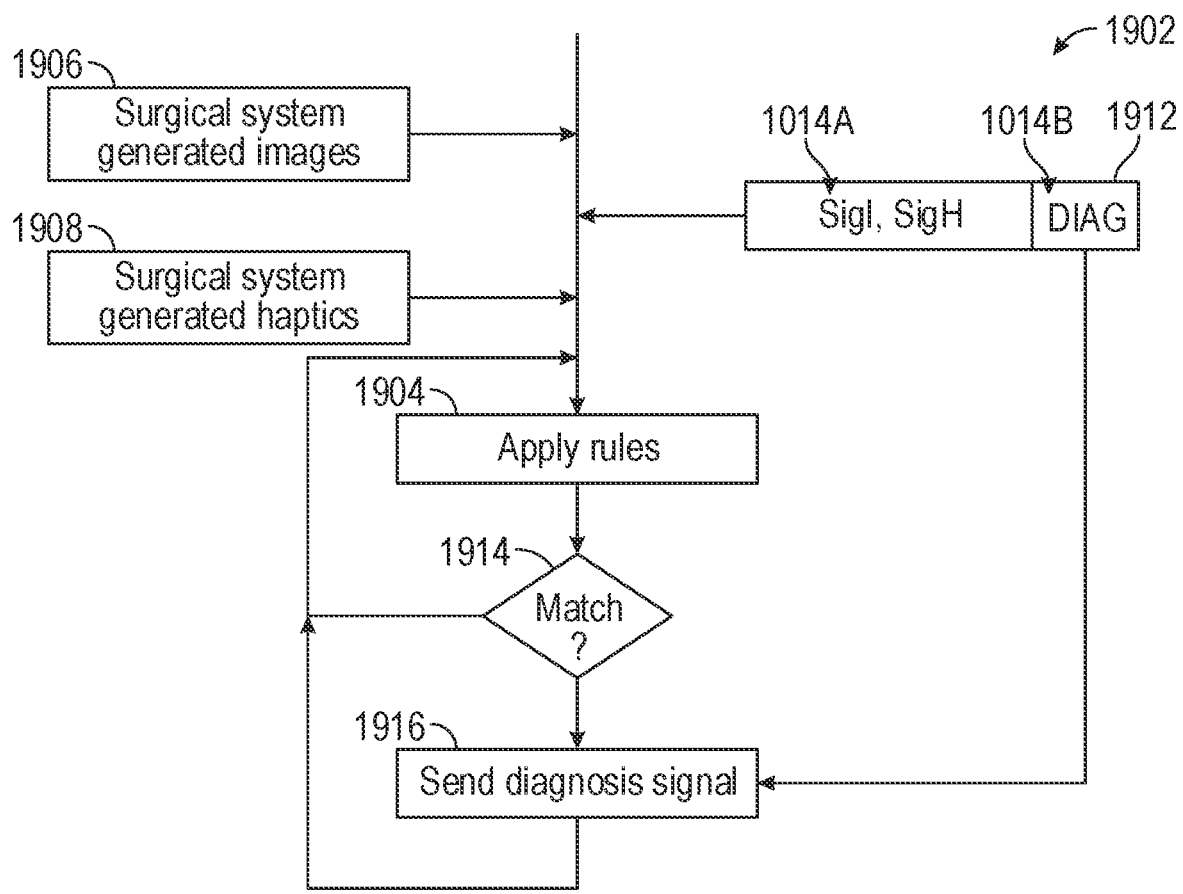
FIG. 19 is an illustrative flow diagram representing a process to produce a diagnosis based at least in part upon anatomical image information and haptic feedback information, in accordance with some embodiments.

FIG. 19 is an illustrative flow diagram representing a process 1902 to produce a diagnosis based at least in part upon anatomical image information and haptic feedback information, in accordance with some embodiments. The computer processor 58 is configured to perform the process 1902 in accordance with some embodiments. During performance of a surgical procedure, a rules block 1904 determines whether to report a diagnosis based upon motion picture images and haptic feedback forces during the surgery, and rules from the second rules information structure 1014.

More particularly, during performance of a surgical procedure using system 10, rules block 1904 receives motion picture image information generated during the surgery and receives haptic feedback information generated during the surgery. The camera 528 captures motion picture information during the surgery. The computer processor 58 at block 1906, provides corresponding image information to the rules block 1904. The haptic feedback force device 39 generates haptic feedback force. The computer processor 58 at block 1908, determines haptic feedback force information based upon the actuation commands and provides the kinematic information to the rules block 1904.

Also, during the surgical procedure, a diagnosis rules storage block 1912 provides to the rules block 1904 image signature information and haptic feedback information from a first rules block portion 1014A of the diagnosis rules information structure 1014. The rules block 1904 compares image and haptic feedback information provided by blocks 1906, 1908, respectively, with associated image signatures (SigI) and haptics feedback signatures (SigH) from the first rules block portion 1014A of the rules diagnosis structure 1014. It will be appreciated that in some embodiments, the computer processor 58 is configured to transform image and haptic feedback information generated by the system 10 into a format suitable for comparing against signature and state information from the first portion 1014A of the diagnosis rules information structure 1014.

Decision module 1914 determines whether a match occurs between the provided image and haptic feedback information and rules information from the first rules portion 1014A of the diagnosis rules information structure 1014. It will be appreciated that in machine learning embodiments a match is determined based upon a range of similarity between the image and haptic information and rules information. Thus, for example, a combination of generated image and generated haptics information that is within some threshold limit of a certain rule is determined to match that rule.

Block 1914, in response to determination of a match between a combination of image, kinematics and system state information and a rule, launches a control signal from within a second rules block 1010B portion of the first control signal rules information structure 1010 that corresponds the matching rule. For example, in response to determination that image and haptic feedback information received during a surgical procedure matches $SigI_2$, and $SigH_2$ of a first portion 1014A of the diagnosis information structure 1014, block 1916 reports on the viewer 31, diagnosis DIAG1 form a second portion of the diagnosis information structure 1014. Thus, a diagnosis during a surgery depends upon actual system information generated during a surgery and information recorded in many prior surgeries. During the process 1902, while no match is detected, decision module 1914 feeds back control flow to the rules block 1904. Similarly, after a diagnosis, flow controls back to the rules block 1904 to continue with comparisons of image and haptics generated during a surgery with rules from the diagnosis rules information structure 1014.

Although illustrative embodiments have been shown and described, a wide range of modification, change and substitution is contemplated in the foregoing disclosure and in some instances, some features of the embodiments may be employed without a corresponding use of other features. For example, in some embodiments, the processor 58 is coupled to a memory device such as storage device 1004 that includes instructions to generate a virtual surgical system that includes a virtual surgical instrument and a virtual surgical instrument actuator. The memory device 1004 includes an instruction set executable on the processor 58 to cause the processor 58 to perform virtual operations. In some embodiments, the virtual operations include receiving user input commands from a user to control movement of a first virtual robotic surgical instrument. The virtual operations further include tracking virtual surgical instrument actuator state of the first virtual robotic instrument during movement of the first virtual robotic surgical instrument in response to the user input commands during a virtual surgical procedure. The virtual operations include recording virtual surgical instrument kinematic information indicative of virtual surgical instrument motion produced within the virtual surgical system during the occurrence of the virtual surgical procedure. The virtual operations include determining respective kinematic signatures associated with respective virtual surgical instrument motions and producing an information structure in a computer readable storage device that associates respective kinematic signatures with respective control signals. The virtual operations further include comparing, during a performance of the virtual surgical procedure within the virtual surgical system, virtual surgical instrument kinematic information during the performance with at least one respective kinematic signature. The virtual operations further include launching, during a performance of the virtual surgical procedure within the virtual surgical system, an associated respective control signal within the virtual surgical system in response to a match between virtual surgical instrument kinematics during the performance and a respective kinematic signature.

In yet another embodiment, a system produces a virtual surgical system that includes an information structure in a computer readable storage device that associates surgical image signatures with control signals. A processor is configured to generate a virtual surgical system. The processor is configured to compare, during a performance of a virtual surgical procedure within the virtual surgical system, surgical images within a surgical scene with at least one surgical image signature. The processor is configured to launch, during the performance of the virtual surgical procedure a control signal within in response to a match between surgical images during the performance and the at least one surgical image signature. The processor is configured to generate a virtual instrument configured to adjust its motion in response to the control signal.

EXAMPLES

Example 1 includes a method for use with a virtual surgical system, the method comprising: for a multiplicity of occurrences of a virtual surgical procedure, recording virtual surgical instrument kinematic information indicative of virtual surgical instrument motion produced within the virtual surgical system during the occurrence of the virtual surgical procedure; determining respective kinematic signatures associated with respective virtual surgical instrument motions; producing an information structure in a computer readable storage device that associates respective kinematic signatures with respective control signals; comparing, during a performance of the virtual surgical procedure within the virtual surgical system, virtual surgical instrument kinematic information during the performance with at least one respective kinematic signature; launching, during a performance of the virtual surgical procedure within the virtual surgical system, an associated respective control signal within the virtual surgical system in response to a match between virtual surgical instrument kinematics during the performance and a respective kinematic signature.

Example 2 includes the method of claim Example 1 further including: in response to the control signal, adjusting speed at which a virtual instrument moves.

Example 3 includes the method of Example 1 further including: in response to the control signal, adjusting a range of motion of a virtual instrument.

Example 4 includes the method of Example 1 further including: in response to the control signal, providing a visual image providing guidance to an operator.

Example 5 includes a method for use with a virtual surgical system, the method comprising: for a multiplicity of occurrences of a virtual surgical procedure within a virtual surgical system, recording images of a surgical scene within the virtual surgical system during the occurrence of the virtual surgical procedure; determining respective surgical image signatures associated with respective images of surgical scenes; producing an information structure in a computer readable storage device that associates respective surgical image signatures with respective control signals; comparing, during a performance of the virtual surgical procedure within the virtual surgical system, surgical images within a surgical scene within the virtual surgical system with at least one respective surgical image signature; launching, during a performance of the virtual surgical procedure within the virtual surgical system, an associated respective control signal within the virtual surgical system in response to a match between surgical images during the performance and a respective surgical image signature.

Example 6 includes the method of Example 5 further including: in response to the control signal, adjusting speed at which a virtual instrument moves.

Example 7 includes the method of Example 5 further including: in response to the control signal, adjusting a range of motion of a virtual instrument.

Example 8 includes the method of Example 5 further including: in response to the control signal, providing a visual image providing guidance to an operator.

Example 9 includes a system to produce a virtual surgical system comprising: an information structure in a computer readable storage device that associates respective kinematic signatures with respective control signals; a processor configured to, generate a virtual surgical system; compare, during a performance of a virtual surgical procedure, virtual instrument kinematic information generated during the virtual surgical procedure with at least one surgical image signature; and launch, during the performance of the virtual surgical procedure a control signal in response to a match between virtual instrument kinematic information generated during the virtual surgical procedure and the at least one surgical image signature; and generate a virtual instrument configured to adjust its motion in response to the control signal.

Example 10 includes the system of Example 9, wherein in response to the control signal, the virtual instrument is configured to adjust speed at which it moves.

Example 11 includes the system of Example 9, wherein in response to the control signal, the virtual instrument is configured to adjust a range of motion of the instrument.

Example 12 includes the system of Example 9, wherein in response to the control signal, the virtual instrument is configured to adjust visual guidance provided to an operator.

Example 13 includes a system to produce a virtual surgical system comprising: an information structure in a computer readable storage device that associates respective surgical image signatures with respective control signals; a processor configured to, generate a virtual surgical system; compare, during a performance of a virtual surgical procedure within the virtual surgical system, surgical images within a surgical scene with at least one surgical image signature; launch, during the performance of the virtual surgical procedure a control signal within in response to a match between surgical images during the performance and the at least one surgical image signature; and generate a virtual instrument configured to adjust its motion in response to the control signal.

Example 14 includes the system of Example 13, wherein in response to the control signal, the virtual instrument is configured to adjust speed at which it moves.

Example 15 includes the system of Example 13, wherein in response to the control signal, the virtual instrument is configured to adjust a range of motion of the instrument.

Example 16 includes the system of Example 13, wherein in response to the control signal, the virtual instrument is configured to adjust visual guidance provided to an operator.

Example 17 includes a method for use with a teleoperated surgical system (surgical system), the method comprising: for a multiplicity of occurrences of a surgical procedure within one or more instances of the surgical system, recording images of a surgical scene within the surgical system during the occurrence of the surgical procedure determining respective surgical image signatures and kinematic signatures associated with respective images of surgical scenes; producing an information structure in a computer readable storage device that associates respective surgical image signatures and kinematic signatures with respective control signals comparing, during a performance of the surgical procedure within an instance of the surgical system, surgical images within a surgical scene within the instance of the surgical system with at least one respective surgical image signature; comparing, during the performance of the surgical procedure within an instance of the surgical system, surgical instrument kinematic information during the performance with at least one respective kinematic signature; launching, during the performance of the surgical procedure within the instance of the surgical system, an associated respective control signal within the surgical system in response to a match between surgical images during the performance and a respective surgical image signature and a match between the surgical instrument kinematics during the performance and a respective kinematic signature.

Example 18 includes a teleoperated surgical system comprising: an information structure in a computer readable storage device respective surgical image signatures and kinematic signatures with respective control signals; a processor configured to, compare, during a performance of a surgical procedure, instrument kinematic information generated during the surgical procedure with at least one kinematic signature; compare, during a performance of a surgical procedure within the surgical system, surgical images within a surgical scene with at least one surgical image signature; and launch a control signal in response to a match between the instrument kinematic information generated during the surgical procedure and the at least one kinematic signature and a match between surgical images within a surgical scene and the at least one surgical image signature.

Example 19 includes the teleoperated surgical system of Example 18, further comprising an instrument configured to adjust its motion in response to the control signal.

The invention claimed is:

1. A teleoperated surgical system comprising:
a surgical instrument;
an actuator coupled to impart motion to the surgical instrument in response to a control signal;
a control signal rules information structure that provides classifications for kinematic information about the surgical system, based upon kinematic information recorded for a multiplicity of prior occurrences of a surgical procedure, and that associates the classifications with control signals;
a processor communicatively coupled to the actuator, to a sensor and to the control signal rules information structure, the processor configured to perform operations comprising:
receiving the kinematic information that indicates one or more of instantaneous velocity, instantaneous acceleration, instantaneous three-dimensional position, current path of motion or predicted path of motion of the surgical instrument;
identifying a classification of the received kinematic information based upon the classifications provided by the control signal rules information structure; and
launching a control signal associated by the control signal rules information structure with the identified classification.

2. The teleoperated surgical system of claim 1,
wherein the processor is configured to perform an operation comprising
transforming the received kinematic information to kinematic signature information.

3. The teleoperated surgical system of claim 2,
wherein identifying a classification of the received kinematic information includes comparing the transformed kinematic information with kinematic signature information within one or more of the classifications provided by the control signal rules information structure.

4. The teleoperated system of claim 3,
wherein in response to the control signal, the surgical system adjusts speed at which the instrument moves.

5. The teleoperated system of claim 3,
wherein in response to the control signal, the surgical system adjusts a range of motion of the instrument.

6. The teleoperated system of claim 3,
wherein in response to the control signal, the surgical system adjusts visual guidance provided to an operator.

7. The teleoperated system of claim 2,
wherein kinematic signatures include respective multidimensional vectors.

8. The teleoperated system of claim 2,
wherein kinematic signatures of the instrument include multidimensional vectors that represent one or more of instantaneous velocity, instantaneous acceleration, instantaneous three-dimensional position, current path of motion and predicted path of motion.

9. The teleoperated system of claim 2,
wherein kinematic signatures include multidimensional vectors that represent one or more of location of anatomical structures, location of an instrument, patient health, type of surgery, and prior motion of the instrument.

10. The system of claim 1,
wherein the control signal includes a surgical instrument end effector control signal.

11. The system of claim 1 further including:
one or more actuators configured to adjust motion of a surgical instrument based upon the launched control signal.

12. The teleoperated system of claim 1 further including:
a camera to capture surgical image information within a surgical scene;
wherein the control signal rules information structure provides classifications for kinematic information about the surgical system and the surgical image information and that associates the classifications with control signals;
wherein the processor is communicatively coupled to the camera, the processor further configured to perform operations comprising:
receiving surgical image information from the camera; and
wherein identifying a classification includes, identifying a classification of a combination of the received kinematic information and the received surgical image information based upon the classifications of combinations kinematic information and image signature information provided by the control signal rules information structure.

13. The teleoperated surgical system of claim 12,
wherein the processor is configured to perform operations comprising
transforming the received kinematic information to kinematic signature information; and
transforming the received surgical image information to surgical image signature information.

14. The teleoperated surgical system of claim 13,
wherein identifying a classification includes, identifying a classification of a combination of the received kinematic information and the received surgical image information includes comparing the transformed kinematic information with kinematic signature information within one or more of the classifications provided by the control signal rules information structure and comparing the transformed received surgical image information with surgical image signature information within one or more of the classifications provided by the control signal rules information structure.

15. The system of claim 13,
wherein kinematic signatures include respective multidimensional vectors; and
wherein motion picture surgical image signatures include multidimensional vectors.

16. The system of claim 13,
wherein surgical image signatures of the instrument include multidimensional vectors that represent one or more of color, texture, and geometry.

17. The system of claim 13,
wherein motion picture surgical image signatures include multidimensional vectors that represent one or more of patient health record information, surgery type, and comparison of anatomical image appearance at different surgical stages.

18. A method for use with a teleoperated surgical system, the method comprising:
recording, for each of a multiplicity of occurrences of a surgical procedure within one or more instances of the surgical system, respective diagnosis data information instances comprising,
  respective images of anatomical tissue within a surgical scene displayed within a viewer of a first instance of the surgical system during a surgical procedure;
  respective surgical instrument control haptics imparted to surgical instrument controls of the first instance of the surgical system in response to forces imparted to the surgical instrument during contact with the anatomical tissue within the surgical scene displayed within a viewer during the surgical procedure;
producing an information structure in a computer readable storage device that associates respective diagnosis data information with respective diagnoses;
selecting a respective diagnosis data information instance;
replaying the recorded images from the selected respective recorded diagnosis data information instance within a viewer of a second instance of the surgical system during a simulation of the surgical procedure;
imparting the recorded surgical instrument control haptics from the selected respective recorded diagnosis data information instance to surgical instrument controls of the second instance of the surgical system during the replaying of the recorded images during the simulation of the surgical procedure.

19. The method of claim 18, wherein the imparted recorded surgical instrument control haptics include a vibrotactile force.

* * * * *